(12) United States Patent
Enzelberger et al.

(10) Patent No.: US 8,273,688 B2
(45) Date of Patent: Sep. 25, 2012

(54) COLLECTION OF HCDR3 REGIONS AND USES THEREFOR

(75) Inventors: Markus Enzelberger, Planegg (DE); Stefanie Thiel, München (DE); Josef Prassler, Germering (DE); Stefanie Urlinger, München (DE); Christine Rothe, Dachau (DE)

(73) Assignee: MorphoSys AG, Martinsried (DE)

( * ) Notice: Subject to any disclaimer, the term of this patent is extended or adjusted under 35 U.S.C. 154(b) by 427 days.

(21) Appl. No.: 12/158,181

(22) PCT Filed: Dec. 15, 2006

(86) PCT No.: PCT/IB2006/004301
§ 371 (c)(1),
(2), (4) Date: Sep. 18, 2008

(87) PCT Pub. No.: WO2008/053275
PCT Pub. Date: May 8, 2008

(65) Prior Publication Data
US 2009/0088346 A1    Apr. 2, 2009

Related U.S. Application Data

(60) Provisional application No. 60/751,633, filed on Dec. 20, 2005.

(51) Int. Cl.
*C40B 40/08* (2006.01)
*C40B 40/10* (2006.01)
*C40B 50/00* (2006.01)

(52) U.S. Cl. ............ 506/17; 506/18; 506/23; 424/133.1

(58) Field of Classification Search ........................ None
See application file for complete search history.

(56) References Cited

U.S. PATENT DOCUMENTS

| | | |
|---|---|---|
| 6,300,064 B1 | 10/2001 | Knappik et al. |
| 6,753,136 B2 | 6/2004 | Lohning |
| 6,828,422 B1 | 12/2004 | Achim et al. |
| 2006/0257937 A1 | 11/2006 | Ladner |

FOREIGN PATENT DOCUMENTS

WO           9708320 A1    3/1997

OTHER PUBLICATIONS

Knappik et al. (Fully synthetic human combinatorial antibody libraries (HuCAL) based on modular consensus frameworks and CDRs randomized with trinucleotides, 2000, Journal of Molecular Biology, vol. 1, pp. 57-86).*
Prassler et al. (J. Molec. Biol. 413:261-278 (2011)).*
Rothe et al. (J. Molec. Biol. 376:1182-1200 (2008)).*
Lee C V et al.: "High-affinity Human Antibodies from Phage-displayed Synthetic Fab Liraries with a Single Framework Scaffold" Journal of Molecular Biology, London, GB vol. 340, No. 5, Jul. 23, 2004, pp. 1073-1093, XP004518119 ISSN: 0022-2836.

Barrios Yvelise et al.: "Length of the antibody heavy chain complementarity determining region 3 as a specificity-determining factor." Journal of Molecular Recognition: JMR Jul.-Aug. 2004, vol. 17, No. 4, Jul. 2004, pp. 332-338, XP002482520 ISSN: 0952-3499.
Chothia C, Lesk AM, Gherardi E, Tomlinson IM, Walter G, Marks JD, Llewelyn MB, Winter G., "Structural repertoire of the human VH segments", J Mol Biol. Oct. 5, 1992; 227 (3):799-817.
Chothia C, Lesk AM, Tramontano A, Levitt M, Smith-Gill SJ, Air G, Sheriff S, Padlan EA, Davies D, Tulip ER, et al. "Conformations of immunoglobulin hypervariable regions", Nature Dec. 21-28, 1989; 342 (6252):877-83.
Collis AV, Brouwer AP, Martin AC. "Analysis of the antigen combining site: correlations between length and sequence composition of the hypervariable loops and the nature of the antigen", J Mol Biol. Jan. 19, 2003; 325(2): 337-54.
Feeney AJ "Predominance of VH-D-JH junctions occurring at sites of short sequence homology results in limited junctional diversity in neonatal antibodies", J Immunol. Jul. 1, 1992; 149(1):222-9.
Hoet et al., Nature Biotech 23:(3) Mar. 2005.
Honegger A, Plückthun A., "Yet another numbering scheme for immunoglobulin variable domains: an automatic modeling and analysis tool." J Mol. Biol. Jun. 8, 2001;309(3):657-70.
Johnson G, Wu TT, "Preferred CDRH3 lengths for antibodies with defined specificities", Int Immunol. Dec. 1998, 10(12)1801-5.
Knappik A, Gel L, Honegger A, Pack P, Fischer M, Wellnhofer G, Hoess A, Wölle J, Plückthun A, Virnekäs B, "Fully synthetic human combinatorial antibody libraries (HuCAL) based on modular consensus frameworks and CDRs randomized with trinucleotides", J Mol Biol. Feb. 11, 2000; 296(1):57-86.
Wu TT, Johnson G, Kabat EA, "Length distribution of CDRH3 in antibodies", Proteins. May 1993; 16(1):1-7.
Tonegawa S, "Somatic generation of antibody diversity", Nature. Apr. 14, 1983;302(5909):575-81.
Zemlin M, Klinger M, Link J, Zemlin C, Bauer K, Engler JA, Schroeder HW Jr, Kirkham PM, Expressed murine and human CDR-H3 intervals of equal length exhibit distinct repertoires that differ in their amino acid composition and predicted range of structures, J Mol Biol. Dec. 5, 2003; 334(4):733-49.
Zemlin M, Schelonka RL, Bauer K, Schroeder HW Jr., Regulation and chance in the ontogeny of B and T cell antigen receptor repertoires Immunol Res. 2002; 26(1-3):265-78.

* cited by examiner

*Primary Examiner* — Lynn Bristol
(74) *Attorney, Agent, or Firm* — MorphoSys AG

(57) ABSTRACT

The present invention is directed to the preparation and use of a collection of antibody heavy chain complementarity determining region 3 ($HCDR_3$) members, where diversity of the collection is a function of the length of the $HCDR_3$ members. The diversity of the collection of $HCDR_3$ regions substantially represents the natural amino acid distribution of $HCDR_3$ in the human repertoire. This natural amino acid distribution can be represented by biasing the complete random distribution of amino acids, accordingly, in the $HCDR_3$ encoding DNA sequence by using trinucleotide mutagenesis (TRIM) technology. A collection of $HCDR_3$ members of the invention each can be comprised within a variable region of an antibody (or fragment thereof) to form a library of synthetic antibodies or antibody fragments. The invention also provides nucleic acid molecules encoding such diverse collection and methods of making and using the same.

7 Claims, 4 Drawing Sheets

Fig. 1a + 1b
Left alignment
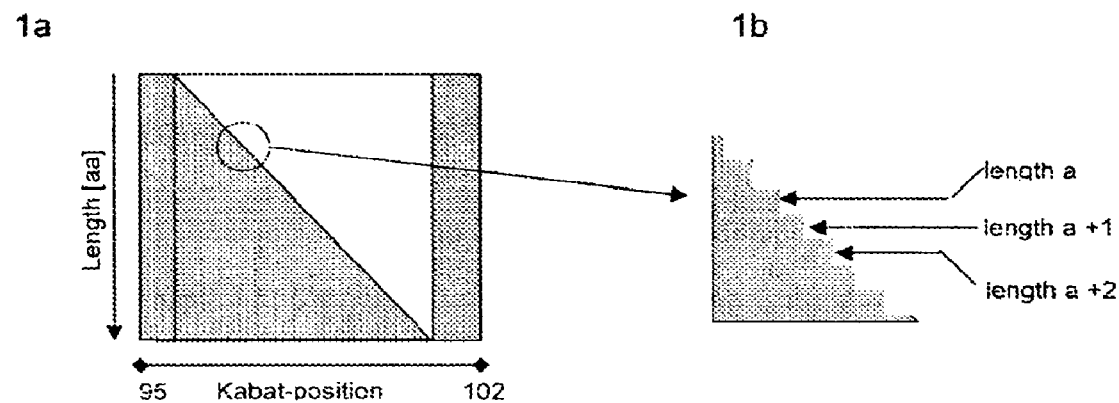
Grey: sequences
White: gap

Fig. 2a + 2b
Right alignment
2a
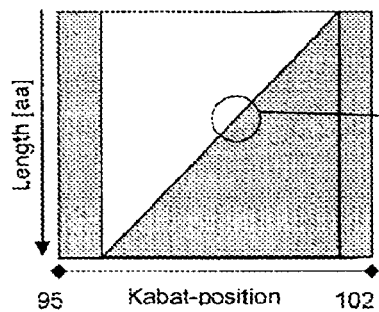
2b
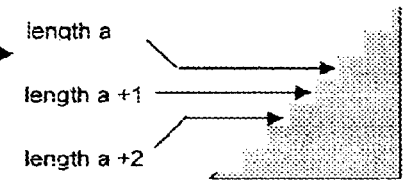
Grey: sequences
White: gap Fig. 3a + 3b + 3c
3a
Flanking-region-Alignment (FR)
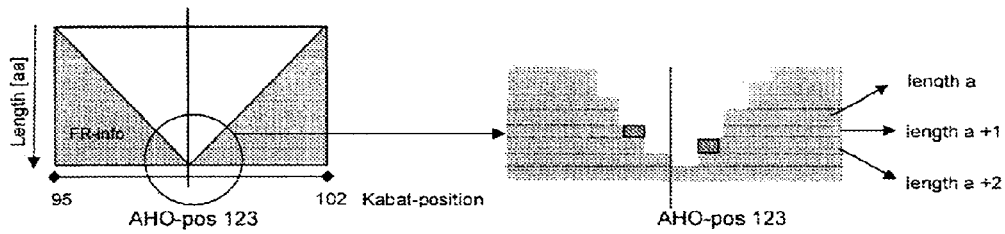
3b
Loop-region-alignment (LR)
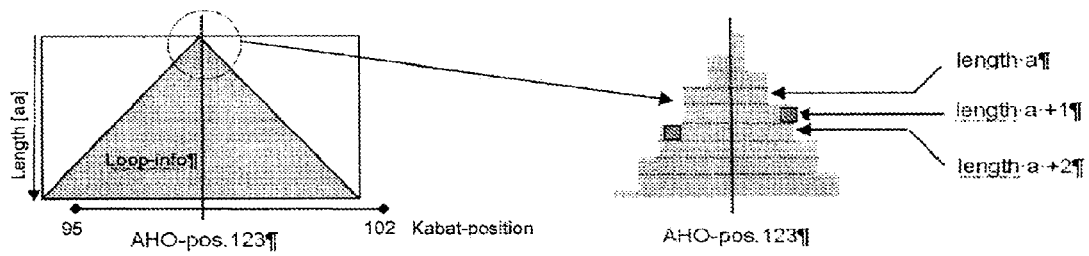
3c
Mixed centred alignment
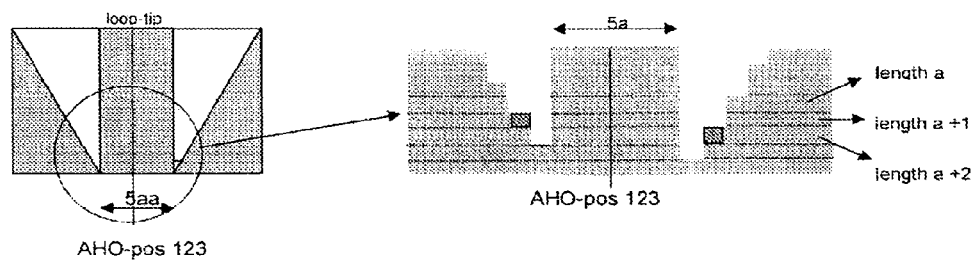
Grey: sequences
White: gap

COLLECTION OF HCDR3 REGIONS AND USES THEREFOR

CROSS-REFERENCE TO RELATED APPLICATION

This application claims the benefit of U.S. provisional application Ser. No. 60/751,633 filed Dec. 20, 2005.

BACKGROUND OF THE INVENTION

The third complementarity-determining region of the immunoglobulin heavy chain (H-CDR3) forms the center of the classical antigen-binding site and often plays a dominant role in determining the specificity and affinity of the antibody. In all known species with an adaptive immune system, H-CDR3 is more diverse than any of the other five CDR regions (H-CDR1, H-CDR2, L-CDR1, L-CDR2 or L-CDR3) that, together, form the outside border of the antigen-binding site (Tonegawa, 1983; Chothia et al., 1989).

It has been found that both the average H-CDR3 length and the range of H-CDR3 lengths, which can have great influence on the range of antigen-binding structures available to the species and thus the function of the antibody repertoire (Johnson & Wu, 1998; Collis et al., 2003), increases from mice to human to cattle (Wu et al., 1993). The diversity of H-CDR3 can also be regulated within a species. For example, in human and mouse, the range of H-CDR3 lengths and the diversity of H-CDR3 increases during ontogeny (Feeney, 1992; Zemlin et al., 2002).

Due to its prominent role in antigen binding, the H-CDR3 region has been used as a vehicle for the introduction of hypervariability in synthetic antibody libraries, which can be used for engineering therapeutic antibodies (Knappik et al., 2000). Randomization of this region with degenerate primers yields enormous sequence diversity, but many, if not most, of these structures are distorted and non-functional (Zemlin et al.; 2003). Therefore, very large synthetic antibody libraries are required to obtain good affinities against a given target.

Zemlin noted that the H-CDR3 regions in humans exhibit a greater range of lengths compared to murine H-CDR3 regions, following Zemlin's analysis of murine and human unique, functional, published H-CDR3 regions. Zemlin also noted that the frequency of certain amino acids changes as the length of the HCDR3 increases. For example, Zemlin reported that the frequency of serine increased with length for sequences of 8-14 amino acid residues, but displayed a mixed patter in sequences longer than 14 amino acid residues.

Recently, Hoet et al., Nature Biotech 23:(3) March 2005, described the construction of an antibody library containing variable heavy (VH) sequences that were partially synthetic, but contained HCDR3 regions captured from human donors. In particular, the portion of the VH chain which does not include the HCDR3 region (FR1-H-CDR1-FR2-H-CDR2-FR3) was made synthetically and incorporated in a VH gene; and the portion of the VH chain which includes the HCDR3 region (H-CDR3-FR4) was derived from naturally occurring human autoimmune patients.

Hoet chose to incorporate HCDR3 sequences captured from human donors on the basis that a similar degree of functional library diversity, and hence quality, could not be achieved through incorporation of a synthetically created HCDR3 region into a VH chain. This was not surprising, given that others have taken the approach of generating so-called focused HCDR3 libraries (see, e.g., published patent application US 2006/0257937A1), where diversity is controlled (by limiting analysis to known V, D and J segments) in an effort to reduce the concentration of non-functional binders, which conventional wisdom has taught is expected to be high in libraries that aim to include as much diversity as possible, thereby making library screening more cumbersome than it needs to be (see patent application '937A1). Indeed, Hoet noted not only that in naturally occurring human antibodies, HCDR3 varies from 4 to over 35 residues and has nonrandom sequence diversity, but also that it is impossible to synthesize DNA encoding both the sequence and the length diversity found in natural H-CDR3 repertoires. To that end, Hoet purports to describe the use of an HCDR3 library taught in patent application '937A1 by noting that germline D segments have been selected to foster proper folding and binding of HCDR3 library members, and that inclusion of D segments in a library is desirable. One practical result of a focused library taught in patent application '937A1, being that it is constructed with a view towards a limited data set, namely known V, D and J segments, is that it fails to achieve optimum diversity or variegation at every amino acid residue.

In contrast to the teachings of Hoet and patent application '937A1, the present invention provides, inter alia, a collection of synthetic human or humanized antibody H-CDR3 regions having a diversity essentially as found in natural H-CDR3 repertoires, mimicking the natural amino acid distribution by biasing the complete random distribution of amino acids in the H-CDR3 encoding DNA sequence. In this sense, the invention provides an antibody library that is constructed in a way that was heretofore deemed impossible to construct.

SUMMARY OF THE INVENTION

The present invention provides for a collection of diverse human or humanized antibody H-CDR3 regions of varying ranges of amino acids, where diversity of the collection is generated by diversifying H-CDR3 regions having a length within a first range of amino acids according to a first diversity factor and by diversifying H-CDR3 regions having a length within a second range of amino acids according to a second diversity factor, where the diversity factors are different.

It is an object of the present invention to provide a collection of diverse human or humanized antibody H-CDR3 regions, where at least a portion of the H-CDR3 regions ranges from about 4 to about 22 amino acids in length.

It is also an object of the present invention to provide a collection of diverse human or humanized antibody H-CDR3 regions, where the first range of amino acids is of about 4 to about 13 amino acids and where the second range of amino acids is of about 14 to about 22 amino acids.

In one aspect, the invention provides for a collection of diverse human or humanized antibody H-CDR3 regions, where diversity of the collection is generated by diversifying H-CDR3 regions having a length within a first range of amino acids according to a first diversity factor, by diversifying H-CDR3 regions having a length within a second range of amino acids according to a second diversity factor and by diversifying H-CDR3 regions having a length within a third range of amino acids according to a third diversity factor, where the diversity factors are different. Such a collection of the present invention may contain diverse human or humanized antibody H-CDR3 regions, where the first range of amino acids is of about 4 to about 9 amino acids and the second range of amino acids is of about 10 to about 16 amino acids, where the third range of amino acids is of about 17 to about 22 amino acids.

In another aspect, the present invention provides for a collection of diverse human or humanized antibody H-CDR3 regions, where diversity of the collection is generated by diversifying H-CDR3 regions having a length within a first range of amino acids according to a first diversity factor, by diversifying H-CDR3 regions having a length within a second range of amino acids according to a second diversity factor, by diversifying H-CDR3 regions having a length within a third range of amino acids according to a third diversity factor, by diversifying H-CDR3 regions having a length within a fourth range of amino acids according to a fourth diversity factor, by diversifying H-CDR3 regions having a length within a fifth range of amino acids according to a fifth diversity factor and by diversifying H-CDR3 regions having a length within a sixth range of amino acids according to a sixth diversity factor, where the diversity factors are different. Such a collection of the present invention may contain diverse human or humanized antibody H-CDR3 regions, where the first range of amino acids is of about 4 to about 6 amino acids, the second range of amino acids is of about 7 to about 9 amino acids, the third range of amino acids is of about 10 to about 12 amino acids, the fourth range of amino acids is of about 13 to about 15 amino acids, the fifth range of amino acids is of about 16 to about 18 amino acids, where the sixth range of amino acids is of about 19 to about 22 amino acids.

In yet another aspect, the present invention provides for a collection of diverse human or humanized antibody H-CDR3 regions, where diversity of the collection is generated by diversifying H-CDR3 regions having a length within a first range of amino acids according to a first diversity factor, by diversifying H-CDR3 regions having a length within a second range of amino acids according to a second diversity factor, by diversifying H-CDR3 regions having a length within a third range of amino acids according to a third diversity factor, by diversifying H-CDR3 regions having a length within a fourth range of amino acids according to a fourth diversity factor, by diversifying H-CDR3 regions having a length within a fifth range of amino acids according to a fifth diversity factor, by diversifying H-CDR3 regions having a length within a sixth range of amino acids according to a sixth diversity factor, by diversifying H-CDR3 regions having a length within a seventh range of amino acids according to a seventh diversity factor, by diversifying H-CDR3 regions having a length within an eighth range of amino acids according to an eighth diversity factor, where the diversity factors are different. Such a collection of the present invention may contain diverse human or humanized antibody H-CDR3 regions, where the first range of amino acids is of about 4 to about 5 amino acids, the second range of amino acids is of about 6 to about 7 amino acids, the third range of amino acids is of about 8 to about 9 amino acids, the fourth range of amino acids is of about 10 to about 11 amino acids, the fifth range of amino acids is of about 12 to about 13 amino acids, the sixth range of amino acids is of about 14 to about 15 amino acids, the seventh range of amino acids is of about 16 to about 17 amino acids, the eighth range of amino acids is of about 18 to about 19 amino acids and where the ninth range of amino acids is of about 20 to about 22 amino acids.

It is also an object of the present invention to provide a collection of diverse human or humanized antibody H-CDR3 regions, where the first range of amino acids is of about 4 to about 8 amino acids, and where the first diversity factor requires that: Alanine has a frequency rate of about 80% at position 1, Arginine has a frequency rate of about 60% at position 2, Glycine has a frequency rate of about 40% at position 3, Aspartic acid has a frequency rate of about 50% at position 7 and Tyrosine has a frequency rate of about 40% at position 8.

In another aspect, the present invention provides for a collection of diverse human or humanized antibody H-CDR3 regions, where the first range of amino acids is of about 9 to about 15 amino acids, and where the first diversity factor requires that: Alanine has a frequency rate of about 90% at position 1, Arginine has a frequency rate of about 70% at position 2, Tyrosine has a frequency rate of about 20% at position 10, Tyrosine has a frequency rate of about 20% at position 11, Tyrosine has a frequency rate of about 30% at position 12, Phenylalanine has a frequency rate of about 60% at position 13, Aspartic acid has a frequency rate of about 80% at position 14 and Tyrosine has a frequency rate of about 40% at position 15.

The present invention provides a collection of diverse human or humanized antibody H-CDR3 regions, where the first range of amino acids is of about 16 to about 22 amino acids, and where the first diversity factor requires that: Alanine has a frequency rate of about 90% at position 1, Arginine has a frequency rate of about 60% at position 2, Aspartic acid has a frequency rate of about 30% at position 3, Glycine has a frequency rate of about 20% at position 4, Arginine has a frequency rate of about 10% at position 5, Arginine has a frequency rate of about 10% at position 6, Tyrosine has a frequency rate of about 20% at position 7, Tyrosine has a frequency rate of about 40% at position 15, Tyrosine has a frequency rate of about 50% at position 16, Tyrosine has a frequency rate of about 50% at position 17, Tyrosine has a frequency rate of about 60% at position 18. Tyrosine has a frequency rate of about 40% at position 19, Methionine has a frequency rate of about 50% at position 20, Aspartic acid has a frequency rate of about 95% at position 21 and Valine has a frequency rate of about 60% at position 22.

In another aspect, the present invention provides a collection of diverse human or humanized antibody H-CDR3 regions, wherein if the amino acid length of an antibody H-CDR3 region is of about 9 to about 15 amino acids, then diversity is generated by a high content of Glycine and Serine within the H-CDR3 region. In the context of the present invention, the term "high content," with respect to an amino acid or a group thereof, is defined as a frequency rate of more than 10% of such amino acid or group thereof.

In yet another aspect, the present invention provides a collection of diverse human or humanized antibody H-CDR3 regions, wherein if the amino acid length of an antibody H-CDR3 region is of about 16 to about 22 amino acids, then diversity is generated by a high content of serine within the H-CDR3 region, a high content of basic amino acids in the end part of the H-CDR3 region, aspartic acid in the front part of the HCDR3 and a high content of aromatic amino acid over the whole H-CDR3 region.

It is also an object of the present invention to provide a collection of diverse human or humanized antibody H-CDR3 regions: wherein if the amino acid length of an antibody H-CDR3 region is 5 amino acids, then the amino acid composition is 60% Alanine, 20% Threonine and a mixture of 0.58% of all naturally occurring amino acids except Cysteine at position 1, 30% Arginine, 30% Lysine, 30% Threonine and a mixture of 0.55% of all naturally occurring amino acids except Cysteine at position 2, 40% Aspartic acid, 40% Phenylalanine and a mixture of 0.58% of all naturally occurring amino acids except Cysteine at position 3, 30% Aspartic acid, 30% Glycine, 30% Methionine and a mixture of 0.63% of all naturally occurring amino acids except Cysteine at position 4 and 30% Tyrosine, 30% Aspartic acid and a mixture of 0.58% of all naturally occurring amino acids except Cysteine at position 5.

It is another object of the present invention to provide a collection of diverse human or humanized antibody H-CDR3 regions, wherein if the amino acid length of an antibody H-CDR3 region is of 12 amino acids, then the amino acid composition is 85% Alanine and 15% of a mixture of Threonine and Valine at position 1, 70% Arginine and 30% of a mixture of Serine, Threonine, Glycine and Alanine at position 2, 20% of a mixture of Alanine, Serine and Tyrosine and 0.63% of all naturally occurring amino acids except Cysteine at position 9, 60% Phenylalanine, 10% Methionine and 0.58% of all naturally occurring amino acids except Cysteine at position 10, 80% Aspartic acid, 5% Glycine and 0.58% of all naturally occurring amino acids except Cysteine at position 11 and 50% Tyrosine, 10% of a mixture of Valine and Isoleucine and 0.63% of all naturally occurring amino acids except Cysteine at position 12.

It is also an object of the present invention to provide a collection of diverse human or humanized antibody H-CDR3 regions, wherein if the amino acid length of an antibody H-CDR3 region is of 20 amino acids, then the amino acid composition is 100% Alanine at position 1, 50% Arginine and 50% Lysine at position 2, 30% Glycine and 0.55% of all naturally occurring amino acids except Cysteine at position 3, 20% Arginine, 20% Glycine, 20% Leucine and 0.63% of all naturally occurring amino acids except Cysteine at position 4, 20% Serine, 20% Threonine, 20% Cysteine and 0.63% of all naturally occurring amino acids except Cysteine at position 14, 95% Aspartic acid at position 21 and 50% Valine and 0.55% of all naturally occurring amino acids except Cysteine at position 22.

The invention also relates to a collection of diverse human or humanized antibody variable heavy chains comprising a collection of diverse human or humanized antibody H-CDR3 regions of varying ranges of amino acids, where diversity of the collection is generated by diversifying H-CDR3 regions having a length within a first range of amino acids according to a first diversity factor and by diversifying H-CDR3 regions having a length within a second range of amino acids according to a second diversity factor.

In another aspect, the present invention also provides a collection of diverse human or humanized antibodies or functional fragments thereof, comprising a collection of human or humanized antibody variable heavy chains that comprises a collection of diverse human or humanized antibody H-CDR3 regions of varying ranges of amino acids according to the present invention.

In yet another aspect, the present invention also provides for a synthetic human or humanized antibody library, comprising a collection of diverse human or humanized antibodies or functional fragments thereof comprising a collection of human or humanized antibody variable heavy chains according to the present invention.

In another embodiment, the present invention relates to a method of preparing a collection of nucleic acid molecules encoding diverse human or humanized H-CDR3 regions, comprising synthesizing a plurality of DNA molecules, wherein each DNA molecule encodes an H-CDR3 region, where the H-CDR3 regions are of varying ranges, wherein DNA molecules that encode H-CDR3 regions of a first range of amino acids are synthesized according to a first diversity factor and wherein DNA molecules encoding H-CDR3 regions of a second range of amino acids are synthesized according to a second diversity factor, and where the diversity factors are different.

The invention also is related to a collection of nucleic acids encoding a collection of diverse human or humanized antibody H-CDR3 regions according to the present invention.

The invention is also related to a collection of nucleic acids encoding a collection of diverse human or humanized antibody H-CDR3 regions of varying ranges of amino acids, wherein diversity of the collection is generated by diversifying H-CDR3 regions having a length within a first range of amino acids according to a first diversity factor and by diversifying H-CDR3 regions having a length within a second range of amino acids according to a second diversity factor, where the diversity factors are different.

It is also an object of the present invention to provide a method of obtaining a collection of diverse human or humanized antibody H-CDR3 regions of varying lengths comprising expressing the collection of nucleic acids.

In the context of the present invention, it is to be understood, that 1 or more amino acid positions in an otherwise diverse H-CDR3 region may be kept constant. The skilled worker will appreciate that for the efficiency of synthesizing mixtures of trinucleotides to introduce diversity within the H-CDR3 regions and for efficiency of cloning the various diversified H-CDR3 regions, it may be desirable to insert one or more constant positions within the H-CDR3 region.

Thus, It is also an object of the present invention to provide a collection of diverse human or humanized H-CDR3 regions, wherein if members of the collection have a length of 4 to 8 amino acids, then the diversity factor(s) that apply to said members having said length of 4 to 8 amino acids define 0, 1, 2 or 3 constant amino acid positions within the H-CDR3 regions of said members having said length. The invention is also related to a collection of diverse human or humanized H-CDR3 regions, wherein if members of the collection have a length of 9 to 10 amino acids, then the diversity factor(s) that apply to said members having said length of 9 to 10 amino acids define 0, 1, 2 or 3 constant amino acid positions within the H-CDR3 regions of said members having said length.

The invention is also related to a collection of diverse human or humanized H-CDR3 regions, wherein if members of the collection have a length of 11 to 13 amino acids, then the diversity factor(s) that apply to said members having said length of 11 to 13 amino acids define 0, 1, 2 or 3 constant amino acid positions within the H-CDR3 regions of said members having said length. It is also an object of the present invention to provide a collection of diverse human or humanized H-CDR3 regions, wherein if members of the collection have a length of 14 amino acids, then the diversity factor(s) that apply to said members having said length of 14 amino acids define 0, 1, 2, 3, 4 or 5 constant amino acid positions within the H-CDR3 regions of said members having said length.

The invention also relates to a collection of diverse human or humanized H-CDR3 regions, wherein if members of the collection have a length of 15 to 16 amino acids, then the diversity factor(s) that apply to said members having said length of 15 to 16 define 0, 1, 2, 3, 4, 5, 6, 7 or 8 constant amino acid positions within the H-CDR3 regions of said members having said length.

It is also an object of the present invention to provide a collection of diverse human or humanized H-CDR3 regions, wherein if members of the collection have a length of 16 to 17 amino acids, then the diversity factor(s) that apply to said members having said length of 16 to 17 amino acids define 0, 1, 2; 3, 4, 5, 6, 7 or 8 constant amino acid positions within the H-CDR3 regions of said members having said length.

The invention also relates to a collection of diverse human or humanized H-CDR3 regions, wherein if members of the collection have a length of 18 amino acids, then the diversity factor(s) that apply to said members having said length of 18 amino acids define 0, 1, 2, 3, 4, 5, 6, 7 or 8 constant amino acid positions within the H-CDR3 regions of said members having said length.

The invention also relates to a collection of diverse human or humanized H-CDR3 regions, wherein if members of the collection have a length of 19 or longer amino acids, then the diversity of said members having said length of 19 or longer amino acids define 0, 1, 2, 3, 4, 5, 6 or 7 constant amino acid positions within the H-CDR3 regions of said members having said length.

SUMMARY OF THE FIGURES

FIG. 1: Left alignment; each step in the "staircase" depicted in FIG. 1b represents the consensus-sequence of on average 380 sequences with one defined HCDR3-length. In the left alignment, different lengths are arranged by entering additional amino acids residues along the diagonal as with an increasing length from the left to the right.

FIG. 2: Right alignment; each step in the "staircase" depicted in FIG. 2b represents the consensus-sequence of, on average, 380 sequences with one defined HCDR3-length. In the right alignment, different lengths are arranged by entering additional amino acids residues along the diagonal as with an increasing length from the right to the left.

FIGS. 3a+3b+3c: Centered alignment (flanking-region, loop-region, mixed-centered); each layer in the figure depicted in the right figure represents the consensus-sequence of on average 380 sequences with one defined HCDR3-length. In the flanking region alignment, different lengths are arranged by entering additional amino acids residues alternating along the diagonals as with an increasing length from the outside middle to the inside (from flanking region towards loop-region). The dark grey squares are examples for new added residues.

DETAILED DESCRIPTION OF THE INVENTION

Figure 4:
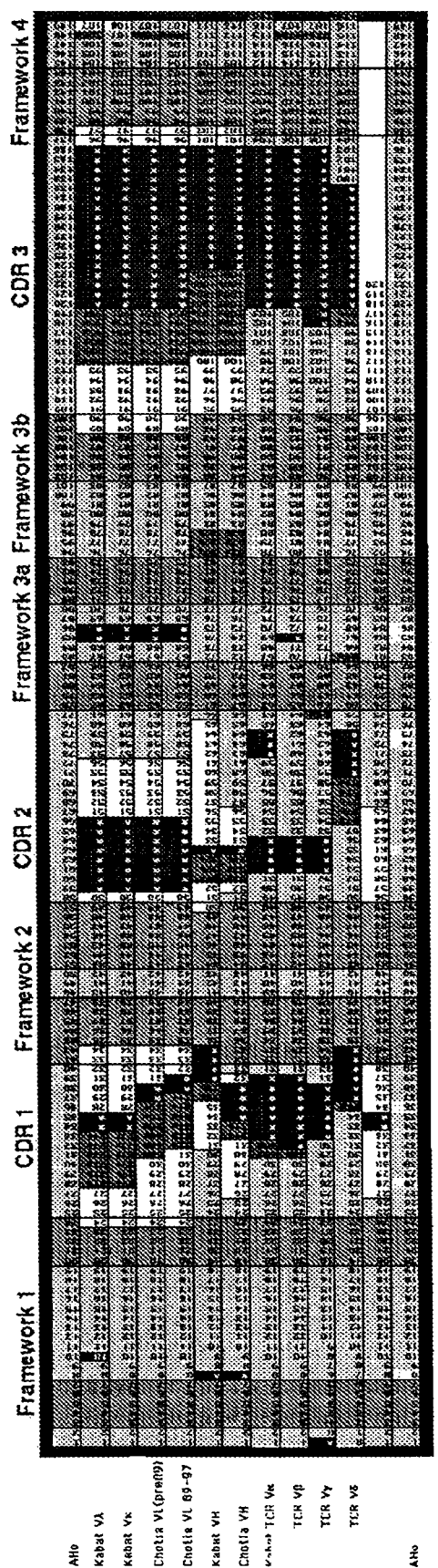
FIG. 4: Example of numbering schemes of antibody variable regions.

In one aspect, the present invention provides, inter alia, a collection of synthetic human or humanized antibody H-CDR3 regions having a diversity essentially as found in natural H-CDR3 repertoires, mimicking the natural amino acid distribution; this is accomplished by biasing the random distribution of amino acids in the H-CDR3 encoding DNA sequence according to the length of the particular H-CDR region.

Instead of just using a limited data set, namely known V, D and J segments, human antibody sequences available from conventionally available databases (e.g. Ig-BLAST) can be analyzed and used as a basis for determining the amino acid distribution in H-CDR3 regions.

In this sense, the invention provides an antibody library that is constructed in a way that was heretofore deemed impossible to construct.

The present invention also provides for a collection of diverse human or humanized antibody H-CDR3 regions of varying lengths of amino acids, wherein diversity of the collection is generated by diversifying H-CDR3 regions having a length within a first range of amino acids according to a first diversity factor and by diversifying H-CDR3 regions having a length within a second range of amino acids according to a second diversity factor.

In the context of the present invention, the term "diversity facto-" is defined as, for any given range of amino acid residues in each H-CDR3 region, the frequency rate at which amino acids appear at one or more given positions in said H-CDR3 region. In the context of the present invention, the "frequency rate" of an amino acid at a given position is defined as the probability of such amino acid of appearing at such position, where frequency can be from 0% to 100%, according to the teachings set forth herein, in naturally occurring human antibodies, the H-CDR3 regions vary from about 4 to 35 amino acids in length. Accordingly the invention contemplates that the length of amino acid residues in each H-CDR3 region may be between 4 and 35, and preferably is 4, 5, 6, 7, 8, 9, 10, 11, 12, 13, 14, 15, 16, 17, 18, 19, 20, 21 or 22 amino acid residues in length, and the range of amino acids to which a particular diversity factor applies can vary, as more fully described herein. The antibodies and/or antibody H-CDR3 regions of the invention, which may be human or humanized, can be used in many contexts, which are more fully described herein.

In one aspect, the present invention provides for diversifying H-CDR3 regions of varying lengths of amino acids according to two to four diversity factors. Accordingly, a collection of diverse human or humanized antibody H-CDR3 regions may be generated by diversifying H-CDR3 regions having a length within a first range of amino acids according to a first diversity factor and by diversifying H-CDR3 regions having a length within a second range of amino acids according to a second diversity factor. In the context of the present invention, the first and second diversity factors are different. The first range of amino acids is of about 4 to about 13 amino acids and the second range of amino acids is of about 14 to about 22 amino acids. Diversity in a collection of diverse human or humanized antibody H-CDR3 regions may be generated by applying: a first diversity factor for H-CDR3 region members having a length of about 4 to about 9 amino acids, a second diversity factor for H-CDR3 region members having a length of about 10 to about 16 amino acids and a third diversity factor for H-CDR3 region members having a length of about 17 to about 22 amino acids. Alternatively, diversity in a collection of diverse human or humanized antibody H-CDR3 regions is generated, for example, by applying: a first diversity factor for H-CDR3 region members having a length of about 4 to about 8 amino acids, a second diversity factor for H-CDR3 region members having a length of about 9 to about 13 amino acids, a third diversity factor for H-CDR3 region members having a length of about 14 to about 18 amino acids, and a fourth diversity factor for H-CDR3 region members having a length of about 19 to about 22 amino acids.

In another aspect, the present invention provides for diversifying H-CDR3 regions of varying lengths of amino acids according to five to seven diversity factors. Diversity in a collection of diverse human or humanized antibody H-CDR3 regions may be generated by applying: a first diversity factor for H-CDR3 region members having a length of about 4 to about 7 amino acids, a second diversity factor for H-CDR3 region members having a length of about 8 to about 11 amino acids, a third diversity factor for H-CDR3 region members having a length of about 12 to about 15 amino acids, a fourth diversity factor for H-CDR3 region members having a length of about 16 to about 19 amino acids and a fifth diversity factor for H-CDR3 region members having a length of about 20 to about 22 amino acids. Diversity in a collection of diverse human or humanized antibody H-CDR3 regions may also be generated by applying: a first diversity factor for H-CDR3 region members having a length of about 4 to about 6 amino acids, a second diversity factor for H-CDR3 region members having a length of about 7 to about 9 amino acids, a third diversity factor for H-CDR3 region members having a length of about 10 to about 12 amino acids, a fourth diversity factor for H-CDR3 region members having a length of about 13 to about 15 amino acids, a fifth diversity factor for H-CDR3 region members having a length of about 16 to about 18 amino acids, and a sixth diversity factor for H-CDR3 region members having a length of about 19 to about 22 amino acids. Diversity in a collection of diverse human or humanized antibody H-CDR3 regions may be generated by applying: a first diversity factor for H-CDR3 region members having a length of about 4 to about 6 amino acids, a second diversity factor for H-CDR3 region members having a length of about 7 to about 9 amino acids, a third diversity factor for H-CDR3 region members having a length of about 10 to about 12 amino acids, a fourth diversity factor for H-CDR3 region members having a length of about 13 to about 15 amino acids, a fifth diversity factor for H-CDR3 region members having a length of about 16 to about 18 amino acids, a sixth diversity factor for H-CDR3 region members having a length of about 19 to about 20 amino acids and a seventh diversity factor for H-CDR3 region members having a length of about 21 to about 22 amino acids.

In another aspect, the present invention provides for diversifying H-CDR3 regions of varying lengths of amino acids according to eight to ten diversity factors. Diversity in a collection of diverse human or humanized antibody H-CDR3 regions can be generated by applying: a first diversity factor for H-CDR3 region members having a length of about 4 to about 6 amino acids, a second diversity factor for H-CDR3 region members having a length of about 7 to about 8 amino acids, a third diversity factor for H-CDR3 region members having a length of about 9 to about 11 amino acids, a fourth diversity factor for H-CDR3 region members having a length of about 12 to about 14 amino acids, a fifth diversity factor for H-CDR3 region members having a length of about 15 to about 16 amino acids, a sixth diversity factor for H-CDR3 region members having a length of about 17 to about 18 amino acids, a seventh diversity factor for H-CDR3 region members having a length of about 19 to about 20 amino acids and an eighth diversity factor for H-CDR3 region members having a length of about 21 to about 22 amino acids. Alternatively, diversity in a collection of diverse human or humanized antibody H-CDR3 regions may be generated by applying: a first diversity factor for H-CDR3 region members having a length of about 4 to about 5 amino acids, a second diversity factor for H-CDR3 region members having a length of about 6 to about 7 amino acids, a third diversity factor for H-CDR3 region members having a length of about 8 to about 9 amino acids, a fourth diversity factor for H-CDR3 region members having a length of about 10 to about 11 amino acids, a fifth diversity factor for H-CDR3 region members having a length of about 12 to about 13 amino acids, a sixth diversity factor for H-CDR3 region members having a length of about 14 to about 15 amino acids, a seventh diversity factor for H-CDR3 region members having a length of about 16 to about 17 amino acids, an eighth diversity factor for H-CDR3 region members having a length of about 18 to about 19 amino acids, and a ninth diversity factor for H-CDR3 region members having a length of about 20 to about 22 amino acids. Diversity in a collection of diverse human or humanized antibody H-CDR3 regions also may be generated by applying: a first diversity factor for H-CDR3 region members having a length of about 4 to about 5 amino acids, a second diversity factor for H-CDR3 region members having a length of about 6 to about 7 amino acids, a third diversity factor for H-CDR3 region members having a length of about 8 to about 9 amino acids, a fourth diversity factor for H-CDR3 region members having a length of about 10 to about 11 amino acids, a fifth diversity factor for H-CDR3 region members having a length of about 12 to about 13 amino acids, a sixth diversity factor for H-CDR3 region members having a length of about 14 to about 15 amino acids, a seventh diversity factor for H-CDR3 region members having a length of about 16 to about 17 amino acids, an eighth diversity factor for H-CDR3 region members having a length of about 18 to about 19 amino acids, a ninth diversity factor for H-CDR3 region members having a length of about 20 to about 21 amino acids and a tenth diversity factor for H-CDR3 region members having a length of about 22 amino acids.

In another aspect, the present invention provides for diversifying H-CDR3 regions of varying lengths of amino acids according to eleven to fourteen diversity factors. Diversity in a collection of diverse human or humanized antibody H-CDR3 regions may be generated by applying: a first diversity factor for H-CDR3 region members having a length of about 4 to about 5 amino acids, a second diversity factor for H-CDR3 region members having a length of about 6 to about 7 amino acids, a third diversity factor for H-CDR3 region members having a length of about 8 amino acids, a fourth diversity factor for H-CDR3 region members having a length of about 9 to about 10 amino acids, a fifth diversity factor for H-CDR3 region members having a length of about 11 amino acids, a sixth diversity factor for H-CDR3 region members having a length of about 12 to about 13 amino acids, a seventh diversity factor for H-CDR3 region members having a length of about 14 to about 15 amino acids, an eighth diversity factor for H-CDR3 region members having a length of about 16 to about 17 amino acids, a ninth diversity factor for H-CDR3 region members having a length of about 18 to about 19 amino acids, a tenth diversity factor for H-CDR3 region members having a length of about 20 amino acids and an eleventh diversity factor for H-CDR3 region members having a length of about 21 to about 22 amino acids. Diversity in a collection of diverse human or humanized antibody H-CDR3 regions also can be generated by applying: a first diversity factor for H-CDR3 region members having a length of about 4 to about 5 amino acids, a second diversity factor for H-CDR3 region members having a length of about 6 amino acids, a third diversity factor for H-CDR3 region members having a length of about 7 amino acids, a fourth diversity factor for H-CDR3 region members having a length of about 8 to about 9 amino acids, a fifth diversity factor for H-CDR3 region members having a length of about 10 amino acids, a sixth diversity factor for H-CDR3 region members having a length of about 11 to about 12 amino acids, a seventh diversity factor for H-CDR3 region members having a length of about 13 amino acids, an eighth diversity factor for H-CDR3 region members having a length of about 14 to about 15 amino acids, a ninth diversity factor for H-CDR3 region members having a length of about 16 to about 17 amino acids, a tenth diversity factor for H-CDR3 region members having a length of about 18 amino acids, an eleventh diversity factor for H-CDR3 region members having a length of about 19 to about 20 amino acids and a twelfth diversity factor for H-CDR3 region members having a length of about 21 to about 22 amino acids. Diversity in a collection of diverse human or humanized antibody H-CDR3 regions may be generated by applying: a first diversity factor for H-CDR3 region members having a length of about 4 to about 5 amino acids, a second diversity factor for H-CDR3 region members having a length of about 6 amino acids, a third diversity factor for H-CDR3 region members having a length of about 7 amino acids, a fourth diversity factor for H-CDR3 region members having a length of about 8 to about 9 amino acids, a fifth diversity factor for H-CDR3 region members having a length of about 10 amino acids, a sixth diversity factor for H-CDR3 region members having a length of about 11 to about 12 amino acids, a seventh diversity factor for H-CDR3 region members having a length of about 13 amino acids, an eight diversity factor for H-CDR3 region members having a length of about 14 to about 15 amino acids, a ninth diversity factor for H-CDR3 region members having a length of about 16 to about 17 amino acids, a tenth diversity factor for H-CDR3 region members having a length of about 18 amino acids, an eleventh diversity factor for H-CDR3 region members having a length of about 19 to about 20 amino acids, a twelfth diversity factor for H-CDR3 region members having a length of about 21 amino acids and a thirteenth diversity factor for H-CDR3 region members having a length of about 22 amino acids. Diversity in a collection of diverse human or humanized antibody H-CDR3 regions alternatively can be generated by applying: a first diversity factor for H-CDR3 region members having a length of about 4 to about 5 amino acids, a second diversity factor for H-CDR3 region members having a length of 6 amino acids, a third factor for H-CDR3 region members having a length of about 7 amino acids, a fourth diversity factor for H-CDR3 region members having a length of about 8 amino acids, a fifth diversity factor for H-CDR3 region members having a length of about 9 amino acids, a sixth diversity factor for H-CDR3 region members having a length of about 10 to about 11 amino acids, a seventh diversity factor for H-CDR3 region members having a length of about 12 amino acids, an eighth diversity factor for H-CDR3 region members having a length of about 13 to about 14 amino acids, a ninth diversity factor for H-CDR3 region members having a length of about 15 to about 16 amino acids, a tenth diversity factor for H-CDR3 region members having a length of about 17 amino acids, an eleventh diversity factor for H-CDR3 region members having a length of about 18 to about 19 amino acids, a twelfth diversity factor for H-CDR3 region members having a length of about 20 amino acids, a thirteenth diversity factor for H-CDR3 region members having a length of about 21 amino acids and a fourteenth diversity factor for H-CDR3 region members having a length of about 22 amino acids.

In yet another aspect, the present invention provides for diversifying H-CDR3 regions of varying lengths of amino acids according to fifteen to seventeen diversity factors. Diversity in a collection of diverse human or humanized antibody H-CDR3 regions may be generated by applying: a first diversity factor for H-CDR3 region members having a length of about 4 to about 5 amino acids, a second diversity factor for H-CDR3 region members having a length of about 6 amino acids, a third diversity factor for H-CDR3 region members having a length of about 7 amino acids, a fourth diversity factor for H-CDR3 region members having a length of about 8 amino acids, a fifth diversity factor for H-CDR3 region members having a length of about 9 amino acids, a sixth diversity factor for H-CDR3 region members having a length of about 10 to about 11 amino acids, a seventh diversity factor for H-CDR3 region members having a length of about 12 amino acids, an eighth diversity factor for H-CDR3 region members having a length of about 13 amino acids, a ninth diversity factor for H-CDR3 region members having a length of about 14 to about 15 amino acids, a tenth diversity factor for H-CDR3 region members having a length of about 16 amino acids, an eleventh diversity factor for H-CDR3 region members having a length of about 17 to about 18 amino acids, a twelfth diversity factor for H-CDR3 region members having a length of about 19 amino acids, a thirteenth diversity factor for H-CDR3 region members having a length of about 20 amino acids, a fourteenth diversity factor for H-CDR3 region members having a length of about 21 amino acids and a fifteenth diversity factor for H-CDR3 region members having a length of about 22 amino acids. Diversity in a collection of diverse human or humanized antibody H-CDR3 regions can be generated by applying: a first diversity factor for H-CDR3 region members having a length of about 4 to about 5 amino acids, a second diversity factor for H-CDR3 region members having a length of about 6 amino acids, a third diversity factor for H-CDR3 region members having a length of about 7 amino acids, a fourth diversity factor for H-CDR3 region members having a length of about 8 amino acids, a fifth diversity factor for H-CDR3 region members having a length of about 9 amino acids, a sixth diversity factor for H-CDR3 region members having a length of about 10 to about 11 amino acids, a seventh diversity factor for H-CDR3 region members having a length of about 12 amino acids, an eighth diversity factor for H-CDR3 region members having a length of about 13 amino acids, a ninth diversity factor for H-CDR3 region members having a length of about 14 amino acids, a tenth diversity factor for H-CDR3 region members having a length of about 15 amino acids, an eleventh diversity factor for H-CDR3 region members having a length of about 16 amino acids, a twelfth diversity factor for H-CDR3 region members having a length of about 17 amino acids, a thirteenth diversity factor for H-CDR3 region members having a length of about 18 to about 19 amino acids, a fourteenth diversity factor for H-CDR3 region members having a length of about 20 amino acids, a fifteenth diversity factor for H-CDR3 region members having a length of about 21 amino acids and a sixteenth diversity factor for H-CDR3 region members having a length of about 22 amino acids. Diversity in a collection of diverse human or humanized antibody H-CDR3 regions may be generated by applying: a first diversity factor for H-CDR3 region members having a length of about 4 amino acids, a second diversity factor for H-CDR3 region members having a length of about 5 amino acids, a third diversity factor for H-CDR3 region members having a length of about 6 to about 7 amino acids, a fourth diversity factor for H-CDR3 region members having a length of about 8 amino acids, a fifth diversity factor for H-CDR3 region members having a length of about 9 amino acids, a sixth diversity factor for H-CDR3 region members having a length of about 10 amino acids, a seventh diversity factor for H-CDR3 region members having a length of about 11 amino acids, an eighth diversity factor for H-CDR3 region members having a length of about 12 amino acids, a ninth diversity factor for H-CDR3 region members having a length of about 13 amino acids, a tenth diversity factor for H-CDR3 region members having a length of about 14 amino acids, an eleventh diversity factor for H-CDR3 region members having a length of about 15 amino acids, a twelfth diversity factor for H-CDR3 region members having a length of about 16 amino acids, a thirteenth diversity factor for H-CDR3 region members having a length of about 17 to about 18 amino acids, a fourteenth diversity factor for H-CDR3 region members having a length of about 19 amino acids, a fifteenth diversity factor for H-CDR3 region members having a length of about 20 amino acids, a sixteenth diversity factor for H-CDR3 region members having a length of about 21 amino acids and a seventeenth diversity factor for H-CDR3 region members having a length of about 22 amino acids.

In another aspect, the present invention provides for diversifying H-CDR3 regions of varying lengths of amino acids according to eighteen to nineteen diversity factors. Diversity in a collection of diverse human or humanized antibody H-CDR3 regions may be generated by applying: a first diversity factor for H-CDR3 region members having a length of about 4 amino acids, a second diversity factor for H-CDR3 region members having a length of about 5 amino acids, a third diversity factor for H-CDR3 region members having a length of about 6 amino acids, a fourth diversity factor for H-CDR3 region members having a length of about 7 amino acids, a fifth diversity factor for H-CDR3 region members having a length of about 8 amino acids, a sixth diversity factor for H-CDR3 region members having a length of about 9 amino acids, a seventh diversity factor for H-CDR3 region members having a length of about 10 amino acids, an eighth diversity factor for H-CDR3 region members having a length of about 11 amino acids, a ninth diversity factor for H-CDR3 region members having a length of about 12 amino acids, a tenth diversity factor for H-CDR3 region members having a length of about 13 amino acids, an eleventh diversity factor for H-CDR3 region members having a length of about 14 amino acids, a twelfth diversity factor for H-CDR3 region members having a length of about 15 amino acids, a thirteenth diversity factor for H-CDR3 region members having a length of about 16 to about 17 amino acids, a fourteenth diversity factor for H-CDR3 region members having a length of about 18 amino acids, a fifteenth diversity factor for H-CDR3 region members having a length of about 19 amino acids, a sixteenth diversity factor for H-CDR3 region members having a length of about 20 amino acids, a seventeenth diversity factor for H-CDR3 region members having a length of about 21 amino acids and an eighteenth diversity factor for H-CDR3 region members having a length of about 22 amino acids. Diversity in a collection of diverse human or humanized antibody H-CDR3 regions also can be generated by applying: a first diversity factor for H-CDR3 region members having a length of about 4 amino acids, a second diversity factor for H-CDR3 region members having a length of about 5 amino acids, a third diversity factor for H-CDR3 region members having a length of about 6 amino acids, a fourth diversity factor for H-CDR3 region members having a length of about 7 amino acids, a fifth diversity factor for H-CDR3 region members having a length of about 8 amino acids, a sixth diversity factor for H-CDR3 region members having a length of about 9 amino acids, a seventh diversity factor for H-CDR3 region members having a length of about 10 amino acids, an eighth diversity factor for H-CDR3 region members having a length of about 11 amino acids, a ninth diversity factor for H-CDR3 region members having a length of about 12 amino acids, a tenth diversity factor for H-CDR3 region members having a length of about 13 amino acids, an eleventh diversity factor for H-CDR3 region members having a length of about 14 amino acids, a twelfth diversity factor for H-CDR3 region members having a length of about 15 amino acids, a thirteenth diversity factor for H-CDR3 region members having a length of about 16 amino acids, a fourteenth diversity factor for H-CDR3 region members having a length of about 17 amino acids, a fifteenth diversity factor for H-CDR3 region members having a length of about 18 amino acids, a sixteenth diversity factor for H-CDR3 region members having a length of about 19 amino acids, a seventeenth diversity factor for H-CDR3 region members having a length of about 20 amino acids, an eighteenth diversity factor for H-CDR3 region members having a length of about 21 amino acids and a nineteenth diversity factor for H-CDR3 region members having a length of about 22 amino acids.

The skilled worker will appreciate that the number of diversity factors can total up to the number of amino acid positions in an H-CDR3 region member having a defined length. Preferably, up to 19 diversity factors is used and collections of diversified H-CDR3 regions of the invention can be combined to form various collections of diversified H-CDR3 regions, either alone or as part of a variable heavy chain domain or a full-length or substantially full-length immunoglobulin chain.

EXAMPLES

The following non-limiting examples more particularly define various embodiments of the invention, by specifying the parameters for certain diversity factors that can apply to H-CDR3 regions having a length within a particular range of amino acids (aa). The skilled worker will appreciate that some deviation in diversity (amino acid frequency) from the below mentioned theoretical designs is permitted without deviating from the scope of the invention, since there might be, for example, a desire to implement certain cloning efficiencies in constructing a library based, at least in part, on such theoretical designs.

Retrieval and Editing of Sequences for Preparation of H-CDR3-Designs:

The data-sets for analysis were obtained from Ig-BLAST on the NCBI-Server. The following file, which contains data-records of Ig-BLAST was downloaded: ftp:/ftp.ncbi.nih.gov/blast/db/FASTA/igSeqProt.gz. In total 40,808 data-records were downloaded, which were either human, mouse or not assigned in the name-tag of the data-entries in FASTA format. By filtering for data with the keyword "human" in the name-tag in MS-Word, 22,500 entries for human antibodies were extracted. Of the 22,500 entries for human antibodies, 13,235 were assigned to heavy chains and 5,490 to light chains. The rest of the antibodies were further assigned to hc, Ic-kappa and Ic-lambda, since no key-words were found in the name-tag. For the heavy chains, a length-dependent H-CDR3 collection was compiled using different worksheets for different lengths in MS-Excel. For the H-CDR3-analysis, 8,886 of 13,235 sequences for the heavy chain could be taken for analysis.

Length-Dependent H-CDR3-Design:

As an example, the following three separate designs according to three diversity factors were generated:

4aa-7aa

8aa-14aa

15aa-23aa

The Y-content at Kabat position 102 shows a decrease over length 8aa-23aa from 50% to 5%, while the V-content at this position increases from 12% to 65%. In addition, the D-content at position 101 increases from 75% to 100%. To implement the findings of the different aa over the length, but without limiting the scope of the present invention, it was decided that 2 different diversity factors are preferred under a loop-based design: one from 8-14aa and another from 15-23aa, while the diversity factor applying to H-CDR3 regions having 4-7aa in length can be according to a left design.

Alignment-Type:

To summarize one design of several aa-lengths, the following types of alignments are representative alternatives for the design of library members containing 8-14aa and 15-23aa (table 1): Alignment to the left, alignment to the right and a symmetrical alignment.

TABLE 1

Types of alignment; the first three positions and the last position are constant amino acid positions of the framework regions flanking the H-CDR3 region.

| Alignment: left | Alignment: right | Alignment: symmetrical |
|---|---|---|

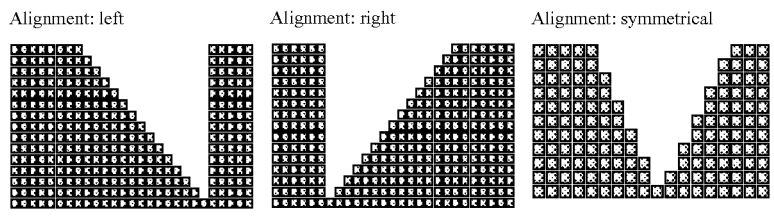

Each step of the "staircase" represents the consensus-sequence of a certain length. The first 3 positions represent parts of the neighboring framework regions: the CAR-region at Kabat-positions 92, 93 and 94 and the W of the beginning of FV4 (WGQG) at Kabat-position 103.

Left Alignment (Table 1+FIG. 1):

The first three positions (Kabat pos 96; 97 and 98) were aligned as block. These positions are at the border between the V- and the D-segment and might be V-encoded (=germline). Thus, these positions might differ in the composition from the rest of the HCDR3 and they were kept separate. Position 96 and 97 differ from other 10H-CDR3 positions, since here the Y-content is decreased, while at position 96, the D-content is raised. The last five positions (Kabat pos l, m, n, 101 and 102) including the dominant FDY-sequences, were aligned as block. Positions 101 and 102 are often J-segment encoded and, thus, show similar amino-acids distributions. First, after filling the first three and the last five positions with aa, the alignment to the left started beginning with Kabat position 99 and successively filling the gap between Kabat pos. 99 and "l".

Right Alignment (Table 1+FIG. 2):

Here also Kabat-positions 96, 97 and 98 as well as Kabat pos l, m, n, 101 and 102 were aligned as block, following the same considerations as described for the alignment left. First after filling the first three and the last five positions with aa, the alignment to the right started beginning with Kabat position "l" and filling successive the gap between Kabat pos. "l" and 99.

Centered Alignment (Table 1+FIGS. 3a, 3b, 3c):

Concerning structural aspects, a symmetrical alignment is a preferred type of alignment and in addition it allows a fast identification of interacting aa in the loop. Here new amino acids are added symmetrical to a certain position. The symmetrical alignment was done centred to AHO-Position 123 as described in "Yet another numbering scheme for immunoglobulin variable domains: an automatic modeling an analysis tool, A. Honegger, A. Plückthun, J. Mol. Biol (2001) 309, 657-670.

Two symmetrical alignments are possible: One alignment, placing a gap at position 123, shifting the sequences into the framework-region and another alignment shifting the sequences toward position 123, with position 123 as symmetrical axis, splitting the sequences into two parts with the same number of aa. The first alignment describes the aa-distribution of the flanking regions (FIG. 3a), while the second alignment describes the loop-tip of the H-CDR3 region (FIG. 3b), although the same sequences can be taken and arranged in another way. For the loop, new amino acids are entered symmetrically at the basis of the loop. In the mixed-centered alignment (FIG. 3c), the sequences were orientated symmetrically to AHO-position 123 but combining the alignments for loop and for flanking regions. A block of 5aa, surrounding position 123, was kept constant, while the other sequences were arranged into the flanking regions. Examples of numbering systems that can be used for antibody variable domains are shown in FIG. 4.

Table 2 shows the result of a centered alignment (flanking-region) for H-CDR3 regions having a length of 4-7aa. "All" describes an equal distribution of all 19aa without Cysteine.

TABLE 2

Centered alignment for H-CDR3 regions with 4-7aa lengths.

| Kabat-pos. | 95 | 96 | 97 | m | n | 101 | 102 |
|---|---|---|---|---|---|---|---|
| AHO-pos. | 109 | 110 | 111 | 112 | 113 | 137 | 138 |
| Name | TRIM1 | TRIM2 | TRIM3 | | | TRIM5 | TRIM6 |
| Design | 25% GD | 10% RGSYA | 25% G | | | 65% D | 50% Y |
| | 5% AEVLRS | 2.6% all | 10% YS | | 15% L | 10% G | 15% V |
| | 1.1% all | | 7.5% AD | | 10% MG | 1.3% all | 10% I |
| | | | 5% T | | 1.8% all | | 1.3% all |
| | | | 2.3% all | | | | |
| natural | 33% G | 11% R | 25% G | 27% G | 31% F | 63% D | 47% Y |
| aa-distribution | 17% D | 10% G | 11% Y | 16% A | 16% L | 7% G | 14% V |
| | 6% A | 10% S | 9% S | 7% S | 11% M | 5% S | 9% I |
| | 6% E | 8% Y | 7% D | 7% Y | 9% G | 4% A | 4% H |
| | 6% V | 7% A | 6% A | 6% V | 4% I | 3% R | 4% P |
| | 5% L | 5% D | 6% T | 5% D | 4% P | 2% E | 3% D |
| | 5% R | 5% H | 5% N | 5% E | 4% S | 2% L | 3% F |
| | 5% S | 5% L | 5% R | 4% T | 3% A | 2% N | 3% L |
| | 2% H | 5% T | 5% W | 3% F | 3% Y | 2% V | 3% S |
| | 2% I | 4% F | 4% L | 3% N | 2% D | 2% Y | 2% G |
| | 2% N | 4% I | 3% P | 3% P | 2% E | 1% H | 2% R |
| | 2% P | 4% N | 3% V | 3% R | 2% R | 1% K | 1% A |
| | 2% T | 4% P | 2% E | 3% W | 2% T | 1% P | 1% N |
| | 2% W | 4% V | 2% F | 2% H | 2% V | 1% T | 1% T |

TABLE 2-continued

Centered alignment for H-CDR3 regions with 4-7aa lengths.

| | | | | | | |
|---|---|---|---|---|---|---|
| 2% Y | 4% W | 2% Q | 2% M | 2% W | 0% C | 0% C |
| 1% K | 3% E | 1% H | 2% Q | 1% C | 0% F | 0% E |
| 1% M | 2% K | 1% I | 1% I | 1% H | 0% I | 0% K |
| 0% C | 2% Q | 1% K | 1% K | 1% K | 0% M | 0% M |
| 0% F | 1% M | 1% M | 1% L | 1% N | 0% Q | 0% Q |
| 0% Q | 0% C | 0% C | 0% C | 0% Q | 0% W | 0% W |

Table 3 shows the result of a centered alignment (loop-region) for H-CDR3 regions having a length of 4-7aa. "All" describes an equal distribution of all 19aa without Cysteine.

TABLE 3

Centered alignment of H-CDR3 regions with 4-7aa lengths.
Result all sequences
Loop regions, H-CDR3, 4aa-7aa

| Kabat-pos. | 95 | 96 | 97 | m | n | 101 | 102 |
|---|---|---|---|---|---|---|---|
| AHO-pos. | 109 | 110 | 111 | 112 | 113 | 137 | 138 |
| Name | TRIM 1 | TRIM 2 | | TRIM 3 | TRIM 4 | TRIM 5 | TRIM 6 |
| Design | 40% G | 10% RSGYA | 20% G | | 25% D | 40% D | 50% Y |
| | 15% D | 5% HLTV | 10% A | | 20% F | 20% Y | 15% V |
| | 5% AELSV | 1.6% all | 7.5% YSFDL | | 10% L | 10% V | 10% I |
| | 1.1% all | | | | 5% GYM | 1.6% all | 1.3% all |
| | | | | | 1.6% all | | |
| natural | 40% G | 12% R | 22% G | 21% G | 26% D | 41% D | 51% Y |
| aa-distribution | 14% D | 11% D | 10% Y | 11% F | 18% F | 21% Y | 15% V |
| | 6% E | 10% G | 7% A | 10% A | 10% L | 8% V | 12% I |
| | 5% A | 10% S | 7% S | 7% D | 6% G | 4% G | 4% D |
| | 5% L | 7% A | 6% D | 7% L | 6% Y | 4% P | 3% P |
| | 5% S | 7% Y | 6% T | 6% M | 5% M | 3% F | 3% S |
| | 5% V | 5% H | 6% W | 6% S | 4% A | 3% H | 2% H |
| | 4% R | 5% L | 5% L | 5% Y | 4% I | 3% I | 2% L |
| | 2% H | 5% T | 5% N | 4% E | 4% R | 3% S | 1% A |
| | 2% I | 5% V | 5% R | 4% P | 4% S | 2% L | 1% F |
| | 2% N | 4% I | 4% F | 4% V | 4% V | 2% N | 1% G |
| | 2% P | 4% N | 4% P | 3% T | 2% P | 2% T | 1% N |
| | 2% T | 3% E | 3% V | 3% W | 1% C | 1% A | 1% R |
| | 2% W | 3% F | 2% E | 2% H | 1% E | 1% R | 1% T |
| | 2% Y | 3% P | 2% M | 2% I | 1% H | 0% C | 0% C |
| | 1% K | 2% K | 2% Q | 2% N | 1% K | 0% E | 0% E |
| | 0% C | 2% W | 1% H | 2% R | 1% N | 0% K | 0% K |
| | 0% F | 1% M | 1% I | 1% K | 1% Q | 0% M | 0% M |
| | 0% M | 1% Q | 1% K | 1% Q | 1% T | 0% Q | 0% Q |
| | 0% Q | 0% C | 0% C | 0% C | 1% W | 0% W | 0% W |

Table 4 shows the result of a left alignment for H-CDR3 regions having a length of 4-7aa. "All" describes an equal distribution of all 19aa without Cysteine.

TABLE 4

Left alignment of H-CDR3 regions with 4-7aa lengths.

| Kabat-pos. | 95 | 96 | 97 | m | n | 101 | 102 |
|---|---|---|---|---|---|---|---|
| AHO-pos. | 109 | 110 | 111 | 112 | 113 | 137 | 138 |
| Name | TRIM 1 | TRIM 2 | TRIM 3 | TRIM 4 | TRIM 5 | TRIM 6 | TRIM 7 |
| Design | 25% GD | 10% RGSY | 25% G | 25% G | 30% F | 65% D | 50% Y |
| | 5% AEVLRS | 5% ADHIT | 10% YSDR | 10% YSA | 15% L | 10% G | 15% V |
| | 1.1% all | 1.8% all | 1.8% all | 2.4% all | 10% MG | 1.3% all | 10% I |
| | | | | | 1.8% all | | 1.3% all |
| natural | 33% G | 12% R | 23% G | 26% G | 29% F | 63% D | 47% Y |
| aa-distribution | 17% D | 12% S | 11% Y | 13% A | 16% L | 7% G | 14% V |
| | 6% A | 10% G | 9% D | 8% Y | 10% M | 5% S | 9% I |
| | 6% E | 8% Y | 8% S | 7% S | 9% G | 4% A | 4% H |
| | 6% V | 6% A | 7% R | 6% T | 4% I | 3% R | 4% P |
| | 5% L | 6% D | 6% A | 4% D | 4% P | 2% E | 3% D |
| | 5% R | 6% H | 6% W | 4% N | 4% Y | 2% L | 3% F |
| | 5% S | 5% I | 5% N | 4% P | 3% A | 2% N | 3% L |
| | 2% H | 5% T | 4% L | 4% V | 3% S | 2% V | 3% S |
| | 2% I | 4% F | 4% T | 4% W | 3% V | 2% Y | 2% G |
| | 2% N | 4% L | 3% E | 3% E | 3% W | 1% H | 2% R |
| | 2% P | 4% N | 3% F | 3% F | 2% D | 1% K | 1% A |

TABLE 4-continued

Left alignment of H-CDR3 regions with 4-7aa lengths.

| | | | | | | |
|---|---|---|---|---|---|---|
| 2% T | 4% V | 3% P | 3% R | 2% E | 1% P | 1% N |
| 2% W | 3% E | 3% V | 2% H | 2% R | 1% T | 1% T |
| 2% Y | 3% P | 2% H | 2% L | 2% T | 0% C | 0% C |
| 1% K | 3% W | 2% Q | 2% M | 1% C | 0% F | 0% E |
| 1% M | 2% K | 1% I | 2% Q | 1% H | 0% I | 0% K |
| 0% C | 2% Q | 1% K | 1% I | 1% K | 0% M | 0% M |
| 0% F | 1% M | 0% C | 1% K | 1% N | 0% Q | 0% Q |
| 0% Q | 0% C | 0% M | 0% C | 0% Q | 0% W | 0% W |

Table 5 shows the result of a right alignment for H-CDR3 regions having a length of 4-7aa. "All" describes an equal distribution of all 19aa without Cysteine.

TABLE 5

Right alignment of H-CDR3 regions with 4-7aa lengths.

| Kabat-pos. | 95 | 96 | 97 | m | n | 101 | 102 |
|---|---|---|---|---|---|---|---|
| AHO-pos. | 109 | 110 | 111 | 112 | 113 | 137 | 138 |
| Name | TRIM 1 | TRIM 2 | TRIM 3 | | TRIM 4 | TRIM 5 | TRIM 6 |
| Design | 30% G | 10% RSGYA | 25% G | | 30% F | 65% D | 50% Y |
| | 20% D | 5% DHIT | 10% YS | | 15% L | 10% G | 15% V |
| | 5% AEVLRS | 1.6% all | 7.5% DRA | | 10% MG | 1.3% all | 10% I |
| | 1.1% all | | 1.8% all | | 1.8% all | | 1.3% all |
| natural | 33% G | 12% R | 23% G | 26% G | 29% F | 63% D | 47% Y |
| aa-distribution | 17% D | 12% S | 11% Y | 13% A | 16% L | 7% G | 14% V |
| | 6% A | 10% G | 9% D | 8% Y | 10% M | 5% S | 9% I |
| | 6% E | 8% Y | 8% S | 7% S | 9% G | 4% A | 4% H |
| | 6% V | 7% A | 7% R | 6% T | 4% I | 3% R | 4% P |
| | 5% L | 6% D | 6% A | 4% D | 4% P | 2% E | 3% D |
| | 5% R | 6% H | 6% W | 4% N | 4% Y | 2% L | 3% F |
| | 5% S | 5% I | 5% N | 4% P | 3% A | 2% N | 3% L |
| | 2% H | 5% T | 4% L | 4% V | 3% S | 2% V | 3% S |
| | 2% I | 4% F | 4% T | 4% W | 3% V | 2% Y | 2% G |
| | 2% N | 4% L | 3% E | 3% E | 3% W | 1% H | 2% R |
| | 2% P | 4% N | 3% F | 3% F | 2% D | 1% K | 1% A |
| | 2% T | 4% V | 3% P | 3% R | 2% E | 1% P | 1% N |
| | 2% W | 3% E | 3% V | 2% H | 2% R | 1% T | 1% T |
| | 2% Y | 3% P | 2% H | 2% L | 2% T | 0% C | 0% C |
| | 1% K | 3% W | 2% Q | 2% M | 1% C | 0% F | 0% E |
| | 1% M | 2% K | 1% I | 2% Q | 1% H | 0% I | 0% K |
| | 0% C | 2% Q | 1% K | 1% I | 1% K | 0% M | 0% M |
| | 0% F | 1% M | 0% C | 1% K | 1% N | 0% Q | 0% Q |
| | 0% Q | 0% C | 0% M | 0% C | 0% Q | 0% W | 0% W |

Table 6 shows the result of a centered alignment (flanking-region) for H-CDR3 regions having a length of 8-14aa. "All" describes an equal distribution of all 19aa without Cysteine. Table 7 shows the result of a centered alignment (loop-region) for H-CDR3 regions having a length of 8-14aa. "All" describes an equal distribution of all 19aa without Cysteine. Table 8 shows the result of a centered alignment (mixed-centered) for H-CDR3 regions having a length of 8-14aa. "All" describes an equal distribution of all 19aa without Cysteine. Table 9 shows the result of a left alignment for H-CDR3 regions having a length of 8-14aa. "All" describes an equal distribution of all 19aa without Cysteine. Table 10 shows the result of a right alignment for H-CDR3 regions having a length of 8-14aa. "All" describes an equal distribution of all 19aa without Cysteine. Table 11 shows the result of a centered alignment (flanking-region) for H-CDR3 regions having a length of 15-23aa. "All" describes an equal distribution of all 19aa without Cysteine. Table 12 shows the result of a centered alignment (loop-region) for H-CDR3 regions having a length of 15-23aa. "All" describes an equal 15 distribution of all 19aa without Cysteine. Table 13 shows the result of a centered alignment (mixed-centered) for H-CDR3 regions having a length of 15-23aa. "All" describes an equal distribution of all 19aa without Cysteine. Table 14 shows the result of a left alignment for H-CDR3 regions having a length of 15-23aa. "All" describes an equal distribution of all 19aa without Cysteine. Table 15 shows the result of a right alignment for H-CDR3 regions having a length of 15-23aa. "All" describes an equal distribution of all 19aa without Cysteine.

TABLE 6

Centered alignment of H-CDR3 regions with 8-14 aa lengths.

| Kabat-pos. | 95 | 96 | 97 | 98 | 99 | 100 | a |
|---|---|---|---|---|---|---|---|
| AHO-pos. | 109 | 110 | 111 | 112 | 113 | 114 | 115 |
| Name | TRIM 1 | TRIM 2 | | | TRIM 3 | | |
| Design | 20% DG | 10% G | 15% GYS | | | | |
| | 8% VEAS | 10% RSLP | 5% DRP | | | | |

TABLE 6-continued

Centered alignment of H-CDR3 regions with 8-14 aa lengths.

|  | 1.5% all | 2.6% all | VALIT 0.8% all |  |  |  |  |
|---|---|---|---|---|---|---|---|
| natural aa-distribution | 22% D | 14% G | 17% G | 17% G | 18% G | 17% G | 16% G |
|  | 19% G | 12% R | 12% S | 13% S | 15% S | 15% S | 15% S |
|  | 9% E | 9% S | 8% Y | 9% Y | 10% Y | 10% Y | 12% Y |
|  | 7% V | 8% L | 7% R | 7% A | 7% A | 8% A | 8% T |
|  | 6% A | 8% P | 6% A | 7% D | 7% T | 7% T | 6% A |
|  | 6% R | 6% T | 6% V | 6% T | 6% V | 6% D | 6% V |
|  | 6% S | 5% A | 5% D | 6% V | 5% D | 5% L | 5% D |
|  | 4% L | 5% V | 5% L | 5% L | 4% L | 5% R | 5% W |
|  | 3% H | 5% Y | 5% P | 5% R | 4% R | 5% V | 4% L |
|  | 3% T | 4% D | 5% T | 4% P | 3% E | 4% P | 4% R |
|  | 2% I | 4% I | 4% I | 4% W | 3% I | 4% W | 3% F |
|  | 2% N | 3% E | 4% W | 3% E | 3% N | 3% N | 3% N |
|  | 2% P | 3% F | 3% E | 3% F | 3% W | 2% E | 3% P |
|  | 2% Q | 3% N | 3% N | 3% I | 2% F | 2% F | 2% E |
|  | 1% C | 3% Q | 2% F | 3% N | 2% P | 2% I | 2% H |
|  | 1% F | 2% H | 2% H | 2% H | 1% C | 1% H | 2% I |
|  | 1% K | 2% K | 2% Q | 2% Q | 1% H | 1% K | 1% C |
|  | 1% M | 2% W | 1% C | 1% C | 1% K | 1% M | 1% K |
|  | 1% W | 1% C | 1% K | 1% K | 1% M | 0% C | 1% M |
|  | 1% Y | 1% M | 1% M | 1% M | 1% Q | 0% Q | 1% Q |

| Kabat-pos. | b | c | d | m | n | 101 | 102 |
|---|---|---|---|---|---|---|---|
| AHO-pos. | 116 | 117 | 118 | 119 | 120 | 137 | 138 |
| Name |  | TRIM 4 |  | TRIM 5 | TRIM 6 | Wobble | TRIM 7 |
| Design | 20% Y |  |  | 20% YA | 50% F | 80% D | 45% Y |
|  | 15% G |  |  | 15% G | 10% ML | 20% A | 15% VI |
|  | 10% S |  |  | 10% W | 1.6% all |  | 10% P |
|  | 2.9% all |  |  | 5% P |  |  | 3% FHLNS |
|  |  |  |  | 2.6% all |  |  |  |
| natural aa-distribution | 15% G | 17% Y | 20% Y | 21% Y | 59% F | 86% D | 45% Y |
|  | 14% Y | 13% G | 16% G | 19% A | 11% M | 2% A | 16% I |
|  | 12% S | 11% S | 11% D | 15% G | 10% L | 2% E | 13% V |
|  | 7% T | 6% A | 8% S | 7% W | 3% I | 2% G | 8% P |
|  | 6% A | 6% L | 7% N | 6% P | 3% Y | 1% H | 4% L |
|  | 6% V | 6% T | 5% T | 6% S | 2% G | 1% L | 3% F |
|  | 5% L | 5% D | 5% W | 3% D | 2% P | 1% N | 3% H |
|  | 5% R | 5% R | 4% A | 3% H | 2% S | 1% P | 3% S |
|  | 4% D | 4% N | 4% R | 3% L | 2% V | 1% Q | 1% D |
|  | 4% N | 4% P | 3% L | 3% R | 1% A | 1% S | 1% N |
|  | 4% P | 4% V | 3% P | 3% T | 1% H | 0% C | 0% A |
|  | 4% W | 4% W | 2% E | 2% E | 1% T | 0% F | 0% C |
|  | 2% C | 3% F | 2% F | 2% F | 1% W | 0% I | 0% E |
|  | 2% E | 2% E | 2% H | 2% N | 0% C | 0% K | 0% G |
|  | 2% F | 2% H | 2% V | 2% V | 0% D | 0% M | 0% K |
|  | 2% H | 2% I | 1% C | 1% C | 0% E | 0% R | 0% M |
|  | 2% I | 2% Q | 1% I | 1% I | 0% K | 0% T | 0% Q |
|  | 2% Q | 1% C | 1% K | 1% Q | 0% N | 0% V | 0% R |
|  | 1% K | 1% K | 1% Q | 0% K | 0% Q | 0% W | 0% T |
|  | 1% M | 1% M | 0% M | 0% M | 0% R | 0% Y | 0% W |

TABLE 7

Centered alignment of H-CDR3 regions with 8-14 aa lengths.

| Kabat-pos. | 95 | 96 | 97 | 98 | 99 | 100 | a | b |
|---|---|---|---|---|---|---|---|---|
| AHO-pos. | 109 | 110 | 111 | 112 | 113 | 114 | 115 | 116 |
| Name | TRIM 1 | TRIM 2 | TRIM 3 |  |  | TRIM 4 |  |  |
| Design | 20% GD | 20% GD | 15% GS | 15% GSY |  |  |  |  |
|  | 9% AEVS | 10% REV | 10% DRV | 7.5% DRALTV |  |  |  |  |
|  | 0.70% | 5% SALP | 5% ALPEITY | 0.5% all |  |  |  |  |
|  |  | 0.5% all | 0.26% all |  |  |  |  |  |
| natural aa-distribution | 25% D | 19% G | 15% G | 17% G | 16% G | 19% G | 18% G | 16% G |
|  | 16% G | 18% D | 10% D | 10% S | 13% S | 14% S | 15% S | 14% Y |
|  | 9% A | 9% R | 10% R | 9% D | 9% Y | 8% Y | 11% Y | 12% S |
|  | 9% E | 7% E | 8% S | 8% R | 7% R | 7% A | 8% A | 7% A |
|  | 6% V | 7% V | 7% V | 7% Y | 6% A | 7% T | 6% D | 6% D |
|  | 5% R | 6% S | 6% A | 6% A | 6% D | 6% D | 6% T | 6% T |
|  | 4% H | 5% A | 6% L | 6% L | 6% L | 5% L | 6% V | 5% L |
|  | 4% L | 5% L | 6% P | 6% T | 6% T | 5% V | 5% L | 5% R |
|  | 4% S | 4% P | 5% E | 6% V | 6% V | 4% R | 5% R | 4% N |
|  | 3% P | 4% T | 4% I | 5% P | 4% I | 4% W | 4% W | 4% V |
|  | 3% T | 3% H | 4% T | 4% E | 4% P | 3% E | 3% F | 4% W |
|  | 2% I | 3% I | 4% Y | 3% I | 3% E | 3% I | 3% N | 3% P |

TABLE 7-continued

Centered alignment of H-CDR3 regions with 8-14 aa lengths.

| | | | | | | | |
|---|---|---|---|---|---|---|---|
| 2% M | 2% F | 3% Q | 2% F | 3% F | 3% N | 3% P | 2% E |
| 2% N | 2% N | 2% F | 2% H | 3% N | 3% P | 2% E | 2% F |
| 1% C | 2% Q | 2% H | 2% K | 3% W | 2% F | 2% H | 2% I |
| 1% F | 2% Y | 2% K | 2% N | 2% H | 2% Q | 2% I | 2% Q |
| 1% K | 1% C | 2% N | 2% Q | 2% Q | 1% H | 1% C | 1% C |
| 1% Q | 1% K | 2% W | 2% W | 1% C | 1% K | 1% K | 1% H |
| 1% W | 1% M | 1% C | 1% C | 1% K | 1% M | 1% M | 1% K |
| 1% Y | 1% W | 1% M | 1% M | 1% M | 0% C | 1% Q | 1% M |

| | | | | | | |
|---|---|---|---|---|---|---|
| Kabat-pos. | c | d | m | n | 101 | 102 |
| AHO-pos. | 117 | 118 | 119 | 120 | 137 | 138 |
| Name | TRIM 5 | TRIM 5 | | TRIM 5 | TRIM 5 | TRIM 5 |
| Design | 20% Y | 15% DYF | | 35% D | 40% D | 45% Y |
| | 15% G | 10% AG | | 25% F | 25% Y | 15% VI |
| | 10% D | 5% WLP | | 15% Y | 10% IV | 10% P |
| | 7.5% ASN | 1.1% all | | 5% IML | 5% PLF | 3% FHLNS |
| | 1.3% all | | | 0.52% | 0.52% all | |
| natural aa-distribution | 18% Y | 17% Y | 22% D | 33% D | 43% D | 39% Y |
| | 13% G | 16% F | 22% F | 23% F | 24% Y | 17% V |
| | 9% A | 11% G | 13% Y | 14% Y | 7% I | 16% I |
| | 8% S | 10% D | 7% A | 6% I | 7% V | 9% P |
| | 7% D | 8% A | 7% G | 5% M | 5% P | 5% L |
| | 6% F | 5% W | 4% L | 4% L | 3% L | 3% H |
| | 5% L | 4% L | 4% M | 3% V | 2% F | 3% S |
| | 5% T | 4% P | 3% P | 2% P | 2% H | 2% F |
| | 5% W | 4% S | 3% W | 2% S | 2% S | 1% D |
| | 4% N | 3% N | 2% H | 1% A | 1% E | 1% N |
| | 4% P | 3% T | 2% I | 1% E | 1% G | 0% A |
| | 3% R | 2% E | 2% S | 1% G | 1% N | 0% C |
| | 3% V | 2% H | 2% V | 1% H | 1% Q | 0% E |
| | 2% E | 2% I | 1% E | 1% N | 0% A | 0% G |
| | 2% H | 2% M | 1% N | 0% C | 0% C | 0% K |
| | 2% I | 2% R | 1% R | 0% K | 0% K | 0% M |
| | 1% C | 2% V | 1% T | 0% Q | 0% M | 0% Q |
| | 1% K | 1% C | 0% C | 0% R | 0% R | 0% R |
| | 1% M | 1% Q | 0% K | 0% T | 0% T | 0% T |
| | 1% Q | 0% K | 0% Q | 0% W | 0% W | 0% W |

TABLE 8

Centered alignment of H-CDR3 regions with 8-14 aa lengths.

| | | | | | | | | |
|---|---|---|---|---|---|---|---|---|
| Kabat-pos. | 95 | 96 | 97 | 98 | 99 | 100 | a | b |
| AHO-pos. | 109 | 110 | 111 | 112 | 113 | 114 | 115 | 116 |
| Name | TRIM 1 | TRIM 2 | TRIM 3 | TRIM 4 | TRIM 3 | TRIM 4 | | |
| Design | 20% DG | 10% G | 15% GYS | 15% GSY | | | | |
| | 8% VEAS | 10% RSLP | 10% AR | 7.5% DAPVT | | | | |
| | 1.5% all | 2.6% all | 5% DP VLIT 0.8% all | 0.9% all | | | | |
| natural aa-distribution | 22% D | 14% G | 16% G | 14% G | 16% G | 19% G | 18% G | 16% G |
| | 19% G | 13% R | 11% S | 13% S | 13% S | 14% S | 15% S | 14% Y |
| | 9% E | 9% S | 8% R | 9% D | 9% Y | 8% Y | 11% Y | 12% S |
| | 7% V | 8% L | 8% Y | 9% Y | 7% R | 7% A | 8% A | 7% A |
| | 6% A | 8% P | 7% V | 8% A | 6% A | 7% T | 6% D | 6% D |
| | 6% R | 6% T | 6% A | 6% P | 6% D | 6% D | 6% T | 6% T |
| | 6% S | 5% A | 6% D | 6% V | 6% L | 5% L | 6% V | 5% L |
| | 4% L | 5% V | 5% L | 5% L | 6% T | 5% V | 5% L | 5% R |
| | 3% H | 5% Y | 5% P | 5% T | 5% V | 4% R | 5% R | 4% N |
| | 3% T | 4% D | 5% T | 4% E | 4% I | 4% W | 4% W | 4% V |
| | 2% I | 4% I | 4% I | 4% I | 4% P | 3% E | 3% F | 4% W |
| | 2% N | 3% E | 3% E | 4% R | 3% E | 3% I | 3% N | 3% P |
| | 2% P | 3% K | 3% F | 3% K | 3% F | 3% N | 3% P | 2% E |
| | 2% Q | 3% Q | 3% W | 2% C | 3% N | 3% P | 2% E | 2% F |
| | 1% C | 2% F | 2% C | 2% F | 3% W | 2% F | 2% H | 2% I |
| | 1% F | 2% H | 2% H | 2% N | 2% H | 2% Q | 2% I | 2% Q |
| | 1% K | 2% N | 2% N | 2% W | 2% Q | 1% H | 1% C | 1% C |
| | 1% M | 2% W | 2% Q | 1% H | 1% C | 1% K | 1% K | 1% H |
| | 1% W | 1% C | 1% C | 1% M | 1% K | 1% M | 1% M | 1% K |
| | 1% Y | 1% M | 1% M | 1% Q | 1% M | 0% C | 1% Q | 1% M |

TABLE 8-continued

Centered alignment of H-CDR3 regions with 8-14 aa lengths.

| Kabat-pos. | c | d | m | n | 101 | 102 |
|---|---|---|---|---|---|---|
| AHO-pos. | 117 | 118 | 119 | 120 | 137 | 138 |
| Name | TRIM 5 | | TRIM 6 | TRIM 7 | TRIM 8 | TRIM 9 |
| Design | 20% Y | | 20% YA | 50% F | 80% D | 45% Y |
|  | 15% G | | 15% G | 10% ML | 20% A | 15% VI |
|  | 10% D | | 10% W | 16% all | | 10% P |
|  | 7.5% ASN | | 5% P | | | 3% FHLNS |
|  | 1.3% all | | 2.6% all | | | |
| natural aa-distribution | 18% Y | 25% Y | 23% Y | 60% F | 86% D | 45% Y |
|  | 13% G | 14% G | 18% A | 11% M | 2% A | 16% I |
|  | 9% A | 12% D | 15% G | 9% L | 2% E | 13% V |
|  | 8% S | 7% N | 8% W | 3% I | 2% G | 8% P |
|  | 7% D | 6% S | 6% P | 3% Y | 1% H | 4% L |
|  | 6% F | 5% W | 4% S | 2% G | 1% L | 3% F |
|  | 5% L | 4% R | 3% H | 2% P | 1% N | 3% H |
|  | 5% T | 4% T | 3% T | 2% S | 1% P | 3% S |
|  | 5% W | 3% L | 2% D | 2% V | 1% Q | 1% D |
|  | 4% N | 3% P | 2% E | 1% A | 1% S | 1% N |
|  | 4% P | 2% A | 2% F | 1% T | 0% C | 0% A |
|  | 3% R | 2% C | 2% L | 1% W | 0% F | 0% C |
|  | 3% V | 2% E | 2% N | 0% C | 0% I | 0% E |
|  | 2% E | 2% F | 2% R | 0% D | 0% K | 0% G |
|  | 2% H | 2% H | 2% V | 0% E | 0% M | 0% K |
|  | 2% I | 2% I | 1% C | 0% H | 0% R | 0% M |
|  | 1% C | 2% Q | 1% I | 0% K | 0% T | 0% Q |
|  | 1% K | 2% V | 0% K | 0% N | 0% V | 0% R |
|  | 1% M | 1% K | 0% M | 0% Q | 0% W | 0% T |
|  | 1% Q | 0% M | 0% Q | 0% R | 0% Y | 0% W |

TABLE 9

Left alignment of H-CDR3 regions with 8-14 aa lengths.

| Kabat-pos. | 95 | 96 | 97 | 98 | 99 | 100 | a |
|---|---|---|---|---|---|---|---|
| AHO-pos. | 109 | 110 | 111 | 112 | 113 | 114 | 115 |
| Name | TRIM 1 | TRIM 2 | | | TRIM 3 | | |
| Design | 20% DG | 10% G | 15% GYS | | | | |
|  | 8% VEAS | 10% RSLP | 5% DRP | | | | |
|  | 1.5% all | 2.6% all | VALIT | | | | |
|  |  |  | 0.8% all | | | | |
| natural aa-distribution | 22% D | 14% G | 17% G | 17% G | 18% G | 17% G | 14% G |
|  | 19% G | 12% R | 12% S | 13% S | 15% S | 14% S | 13% S |
|  | 9% E | 9% S | 8% Y | 9% Y | 10% Y | 11% Y | 13% Y |
|  | 7% V | 8% L | 7% R | 7% A | 7% A | 7% A | 8% T |
|  | 6% A | 8% P | 6% A | 7% D | 7% D | 7% T | 6% A |
|  | 6% R | 6% T | 6% V | 6% T | 6% V | 6% D | 6% L |
|  | 6% S | 5% A | 5% D | 6% V | 5% D | 6% L | 6% V |
|  | 4% L | 5% V | 5% L | 5% L | 4% L | 5% V | 5% D |
|  | 3% H | 5% Y | 5% P | 5% R | 4% R | 4% P | 5% R |
|  | 3% T | 4% D | 5% T | 4% P | 3% E | 4% W | 4% P |
|  | 2% I | 4% I | 4% I | 3% E | 3% I | 4% W | 4% W |
|  | 2% N | 3% E | 4% W | 3% F | 3% N | 3% N | 3% F |
|  | 2% P | 3% F | 3% E | 3% I | 3% W | 2% E | 3% N |
|  | 2% Q | 3% N | 3% N | 3% W | 2% F | 2% F | 2% E |
|  | 1% C | 3% Q | 2% F | 2% H | 2% P | 2% I | 2% I |
|  | 1% F | 2% H | 2% H | 2% H | 1% C | 1% H | 2% Q |
|  | 1% K | 2% K | 2% Q | 2% Q | 1% H | 1% K | 1% C |
|  | 1% M | 2% W | 1% C | 1% C | 1% K | 1% M | 1% H |
|  | 1% W | 1% C | 1% K | 1% K | 1% M | 1% Q | 1% K |
|  | 1% Y | 1% M | 1% M | 1% M | 1% Q | 0% C | 1% M |

| Kabat-pos. | b | c | d | m | n | 101 | 102 |
|---|---|---|---|---|---|---|---|
| AHO-pos. | 116 | 117 | 118 | 119 | 120 | 137 | 138 |
| Name | | TRIM 4 | | TRIM 5 | TRIM 6 | Wobble | TRIM 7 |
| Design | 20% Y | | | 20% YA | 50% F | 80% D | 45% Y |
|  | 15% G | | | 15% G | 10% ML | 20% A | 15% VI |
|  | 10% S | | | 10% W | 1.6% all | | 10% P |
|  | 2.9% all | | | 5% P | | | 3% FHLNS |
|  |  | | | 2.6% all | | | |
| natural aa-distribution | 17% Y | 22% Y | 20% Y | 21% Y | 59% F | 86% D | 45% Y |
|  | 13% G | 13% G | 17% G | 19% A | 11% M | 2% A | 16% I |
|  | 12% S | 10% S | 11% D | 15% G | 10% L | 2% E | 13% V |
|  | 6% A | 6% A | 8% S | 7% W | 3% I | 2% G | 8% P |
|  | 6% T | 6% L | 7% N | 6% P | 3% Y | 1% H | 4% L |
|  | 5% L | 5% P | 5% W | 6% S | 2% G | 1% L | 3% F |

TABLE 9-continued

Left alignment of H-CDR3 regions with 8-14 aa lengths.

| | | | | | | |
|---|---|---|---|---|---|---|
| 4% D | 5% T | 4% A | 3% D | 2% P | 1% N | 3% H |
| 4% N | 4% D | 4% R | 3% H | 2% S | 1% P | 3% S |
| 4% P | 4% R | 4% T | 3% L | 2% V | 1% Q | 1% D |
| 4% R | 4% V | 3% L | 3% R | 1% A | 1% S | 1% N |
| 4% V | 4% W | 2% E | 3% T | 1% H | 0% C | 0% A |
| 4% W | 3% F | 2% F | 3% T | 1% T | 0% F | 0% C |
| 3% F | 3% I | 2% H | 2% F | 1% W | 0% I | 0% E |
| 2% C | 3% N | 2% P | 2% N | 0% C | 0% K | 0% G |
| 2% E | 2% E | 2% V | 2% V | 0% D | 0% M | 0% K |
| 2% H | 2% H | 1% C | 1% C | 0% E | 0% R | 0% M |
| 2% I | 1% C | 1% I | 1% I | 0% K | 0% T | 0% Q |
| 2% K | 1% K | 1% K | 1% Q | 0% N | 0% V | 0% R |
| 2% Q | 1% M | 1% Q | 0% K | 0% Q | 0% W | 0% T |
| 1% M | 1% Q | 0% M | 0% M | 0% R | 0% Y | 0% W |

TABLE 10

Right alignment of H-CDR3 regions with 8-14 aa lengths.

| Kabat-pos. | 95 | 96 | 97 | 98 | 99 | 100 | a | b |
|---|---|---|---|---|---|---|---|---|
| AHO-pos. | 109 | 110 | 111 | 112 | 113 | 114 | 115 | 116 |
| Name | TRIM 1 | TRIM 2 | | | TRIM 3 | | | |
| Design | 20% DG | 10% G | 15% GYS | | | | | |
| | 8% VEAS | 10% RSLP | 5% DRP | | | | | |
| | 1.5% all | 2.6% all | VALIT | | | | | |
| | | | 0.8% all | | | | | |
| natural aa-distribution | 22% D | 14% G | 16% G | 14% G | 16% G | 15% G | 19% G | 17% G |
| | 19% G | 12% R | 11% S | 11% S | 13% S | 15% S | 14% S | 14% S |
| | 9% E | 9% S | 9% R | 9% Y | 11% Y | 8% Y | 10% Y | 11% Y |
| | 7% V | 8% L | 7% V | 7% D | 7% A | 7% A | 7% A | 7% A |
| | 6% A | 8% P | 7% Y | 6% A | 6% R | 7% D | 6% T | 7% T |
| | 6% R | 6% T | 6% A | 6% L | 6% T | 7% T | 6% V | 6% V |
| | 6% S | 5% A | 6% D | 6% P | 6% V | 6% V | 5% D | 5% D |
| | 4% L | 5% V | 6% P | 6% R | 5% D | 5% L | 5% L | 5% R |
| | 3% H | 5% Y | 5% L | 6% T | 5% L | 5% R | 4% R | 4% L |
| | 3% T | 4% D | 5% T | 6% V | 4% I | 4% W | 4% W | 4% P |
| | 2% I | 4% I | 4% E | 4% E | 4% P | 3% E | 3% F | 4% W |
| | 2% N | 3% E | 4% I | 4% I | 3% F | 3% I | 3% I | 3% N |
| | 2% P | 3% F | 3% F | 3% W | 2% C | 3% N | 3% N | 2% E |
| | 2% Q | 3% N | 2% C | 2% C | 2% E | 3% P | 3% P | 2% F |
| | 1% C | 3% Q | 2% H | 2% F | 2% H | 2% F | 2% E | 2% I |
| | 1% F | 2% H | 2% M | 2% H | 2% N | 2% Q | 2% H | 1% C |
| | 1% K | 2% K | 2% N | 2% K | 2% Q | 1% H | 1% C | 1% H |
| | 1% M | 2% W | 2% W | 2% N | 2% W | 1% K | 1% K | 1% K |
| | 1% W | 1% C | 1% K | 2% Q | 1% K | 1% M | 1% M | 1% M |
| | 1% Y | 1% M | 1% Q | 1% M | 1% M | 0% C | 1% Q | 1% Q |

| Kabat-pos. | c | d | m | n | 101 | 102 |
|---|---|---|---|---|---|---|
| AHO-pos. | 117 | 118 | 119 | 120 | 137 | 138 |
| Name | TRIM 4 | | TRIM 5 | TRIM 6 | Wobble | TRIM 7 |
| Design | 15% GS | | 20% YA | 50% F | 80% D | 45% Y |
| | 7.5% DATRV | | 15% G | 10% ML | 20% A | 15% VI |
| | 1.7% all | | 10% W | 1.6% all | | 10% P |
| | | | 5% P | | | 3% FHLNS |
| | | | 2.6% all | | | |
| natural aa-distribution | 15% G | 20% Y | 21% Y | 59% F | 86% D | 45% Y |
| | 15% Y | 17% G | 19% A | 11% M | 2% A | 16% I |
| | 12% S | 11% D | 15% G | 10% L | 2% E | 13% V |
| | 7% A | 8% S | 7% W | 3% I | 2% G | 8% P |
| | 6% L | 7% N | 6% P | 3% Y | 1% H | 4% L |
| | 6% T | 5% W | 6% S | 2% G | 1% L | 3% F |
| | 5% D | 4% A | 3% D | 2% P | 1% N | 3% H |
| | 5% R | 4% R | 3% H | 2% S | 1% P | 3% S |
| | 5% V | 4% T | 3% L | 2% V | 1% Q | 1% D |
| | 4% N | 3% L | 3% R | 1% A | 1% S | 1% N |
| | 4% P | 2% E | 3% T | 1% H | 0% C | 0% A |
| | 4% W | 2% F | 2% E | 1% T | 0% F | 0% C |
| | 3% F | 2% H | 2% F | 1% W | 0% I | 0% E |
| | 2% E | 2% P | 2% N | 0% C | 0% K | 0% G |
| | 2% H | 2% V | 2% V | 0% D | 0% M | 0% K |
| | 2% I | 1% C | 1% C | 0% E | 0% R | 0% M |
| | 2% Q | 1% I | 1% I | 0% K | 0% T | 0% Q |

TABLE 10-continued

Right alignment of H-CDR3 regions with 8-14 aa lengths.

| | | | | | |
|---|---|---|---|---|---|
| 1% C | 1% K | 1% Q | 0% N | 0% V | 0% R |
| 1% K | 1% Q | 0% K | 0% Q | 0% W | 0% T |
| 1% M | 0% M | 0% M | 0% R | 0% Y | 9% W |

TABLE 11

Centered alignment of H-CDR3 regions with 15-23 aa lengths

| Kabat-pos. | 95 | 96 | 97 | 98 | 99 | 100 | a | b | c | d | e | f |
|---|---|---|---|---|---|---|---|---|---|---|---|---|
| AHO-pos. | 109 | 110 | 111 | 112 | 113 | 114 | 115 | 116 | 117 | 118 | 119 | 120 |
| Name | TRIM1 | TRIM2 | | | | TRIM3 | | | | TRIM4 | | TRIM5 |
| Design | 20% DG | 10% G | 15% GYS | | | | | | 15% GSY | | | 15% GYS |
| | 8% VEAS | 10% RSLP | 5% DRP | | | | | | 7.5% RVA | | | 7.5% ILR |
| | 1.5% all | 2.6% all | VALIT | | | | | | | | | 1.7% all |
| | | | 0.8% all | | | | | | | | | |
| natural aa-distribution | 25% D | 15% G | 15% G | 15% YG | 15% GY | 15% SG | 20% S | 15% GS | 15% GS | 15% GS | 15% SY | 15% GYS |
| | 20% G | 10% RPLS | 10% YRS | 10% SDR | 10% SD | 10% YDV | 15% G | 10% YTV | 10% YRV | 10% YA | 10% GLT | 10% IL |
| | 10% AEV | 5% A | 6% L | 6% V | 6% R | 6% A | 10% YV | 6% D | 6% A | 6% I | 6% R | 6% R |
| | 6% S | 5% V | 6% P | 5% I | 6% T | 6% T | 6% D | 6% R | 5% T | 6% L | 5% A | 4% A |
| | 4% L | 4% D | 6% V | 5% L | 6% V | 4% F | 6% T | 5% A | 4% D | 6% V | 5% I | 4% F |
| | 4% R | 4% I | 5% A | 5% P | 4% I | 4% I | 5% A | 5% W | 4% L | 5% T | 5% V | 4% P |
| | 3% H | 4% Y | 5% I | 5% T | 5% P | 4% C | 4% L | 4% I | 4% P | 4% C | 4% W | 4% V |
| | 2% I | 3% E | 5% T | 4% A | 4% F | 4% R | 4% I | 4% L | 4% W | 4% D | 3% D | 3% D |
| | 2% P | 3% F | 4% D | 3% C | 4% I | 4% W | 4% L | 4% P | 3% F | 4% F | 3% F | 3% M |
| | 2% Q | 3% H | 3% E | 3% F | 4% L | 4% L | 4% R | 3% C | 3% I | 4% W | 3% P | 3% T |
| | 2% T | 3% K | 2% C | 2% E | 4% P | 3% P | 4% W | 3% F | 2% C | 3% P | 2% C | 1% C |
| | 1% F | 3% Q | 2% F | 2% H | 3% E | 2% C | 3% N | 3% N | 2% E | 3% R | 2% H | 1% E |
| | 1% K | 3% T | 2% H | 2% K | 3% N | 2% E | 3% P | 2% E | 2% N | 2% E | 2% M | 1% H |
| | 1% M | 2% M | 2% K | 2% N | 2% M | 1% M | 2% C | 2% H | 1% H | 1% H | 2% Q | 1% N |
| | 1% N | 2% N | 2% N | 2% Q | 2% Q | 1% H | 2% E | 1% K | 1% K | 1% K | 1% E | 1% Q |
| | 1% W | 2% W | 2% Q | 2% W | 2% W | 1% K | 1% H | 1% M | 1% Q | 1% N | 1% N | 1% W |
| | 1% Y | 1% C | 2% W | 1% M | 1% H | 1% Q | 1% K | 1% Q | 0% M | 1% Q | 0% K | 0% K |
| | 0% C | | 1% M | | 1% K | | 1% M | | | 0% M | | |
| | | | | | | | 1% Q | | | | | |

| | Kabat-pos. | g | h | i | j | k | l | new | m | n | 101 | 102 |
|---|---|---|---|---|---|---|---|---|---|---|---|---|
| | AHO-pos. | 121 | 122 | 123 | 124 | 125 | 126 | 127 | 128 | 129 | 137 | 138 |
| | Name | | TRIM5 | | TRIM6 | | TRIM7 | TRIM8 | TRIM9 | TRIM10 | wobble | TRIM11 |
| | Design | | | 25% Y | | 35% Y | | 40% Y | 30% G | 50% F | 80% D | 40% V |
| | | | | 10% GS | | 10% SG | | 10% GDN | 20% YA | 30% M | 20% A | 20% Y |
| | | | | 5% RPD | | 5% PRTA | | 1.6% all | 10% W | 10% L | (A for peptide-binders; comment AHO) | 10% IP |
| | | | | 2.1% all | | 1.3% all | | | 5% P | 0.5% all | | 4% FHLMS |
| | | | | | | | | | 0.8% all | | | |
| | natural aa-distribution | 20% G | 15% YG | 20% Y | 25% Y | 35% Y | 40% Y | 40% Y | 30% G | 50% F | 95% D | 40% V |
| | | 15% YSR | 10% ST | 15% G | 10% GS | 10% GS | 10% SG | 10% GDN | 25% Y | 35% M | 1% E | 25% Y |
| | | 6% I | 6% L | 10% S | 6% P | 6% P | 5% P | 4% S | 20% A | 10% L | 1% G | 10% IP |
| | | 6% L | 6% P | 6% R | 5% R | 5% R | 4% W | 4% P | 10% W | 2% I | 1% Q | 5% L |
| | | 5% V | 6% R | 5% D | 5% T | 4% A | 4% A | 3% R | 4% P | 2% V | 0% A | 2% F |
| | | 4% A | 6% V | 5% P | 4% A | 4% L | 4% F | 2% A | 2% F | 1% G | 0% C | 2% H |
| | | 4% C | 5% A | 5% T | 4% C | 4% T | 4% L | 2% E | 2% H | 1% P | 0% F | 2% S |
| | | 4% E | 4% D | 5% V | 4% D | 4% N | 2% F | 2% S | 2% S | 1% S | 0% H | 1% M |
| | | 4% T | 3% C | 4% A | 4% L | 3% F | 4% R | 2% H | 2% T | 1% Y | 0% I | 0% A |
| | | 3% F | 3% F | 4% L | 4% V | 3% D | 3% D | 2% L | 1% D | 0% A | 0% K | 0% C |
| | | 3% P | 3% I | 4% N | 3% N | 2% C | 3% H | 2% P | 1% I | 0% C | 0% L | 0% D |
| | | 2% K | 3% N | 3% F | 2% E | 2% D | 3% V | 2% T | 1% L | 0% D | 0% M | 0% E |
| | | 2% N | 2% E | 3% I | 2% F | 2% H | 2% C | 1% C | 1% N | 0% E | 0% N | 0% G |
| | | 2% W | 2% H | 2% C | 2% H | 2% I | 2% E | 1% I | 1% R | 0% H | 0% P | 0% K |
| | | 1% D | 2% K | 2% E | 2% I | 2% N | 2% I | 1% K | 1% V | 0% K | 0% R | 0% N |
| | | 1% H | 2% Q | 2% K | 2% Q | 2% V | 2% I | 1% V | 0% C | 0% N | 0% S | 0% Q |
| | | 1% M | 2% W | 2% Q | 2% W | 2% W | 1% V | 0% M | 0% E | 0% Q | 0% T | 0% R |
| | | 1% Q | 1% M | 2% W | 1% K | 1% K | 1% K | 0% Q | 0% K | 0% R | 0% V | 0% T |
| | | | | 1% H | 0% M | 0% M | 0% M | | 0% M | 0% T | 0% W | 0% W |
| | | | | 1% M | | | | | 0% Q | 0% W | 0% Y | 0% Y |

TABLE 12

Centered alignment of H-CDR3 regions with 15-23 aa lengths

| Kabat-pos. | 95 | 96 | 97 | 98 | 99 | 100 | a | b | c | d | e | f |
|---|---|---|---|---|---|---|---|---|---|---|---|---|
| AHO-pos. | 109 | 110 | 111 | 112 | 113 | 114 | 115 | 116 | 117 | 118 | 119 | 120 |
| Name | TRIM1 | | TRIM2 | | | TRIM3 | | | TRIM4 | | | TRIM5 |
| Design | 35% D<br>20% G<br>10% VSE<br>0.8% all | 15% DG<br>10% ALR<br>7.5% SV<br>1.3% all | | | 15% GSY<br>10% RPD<br>1.3% all | | | 15% SG<br>10% DYV<br>5% ALTR<br>1.1% all | | | 15% GSY<br>5% RAT<br>VDL<br>1.3% all | |
| natural aa-distribution | 35% D<br>20% G<br>10% VSE<br>6% A<br>4% H<br>4% L<br>2% Q<br>2% R<br>1% F<br>1% K<br>1% N<br>1% T<br>0% C<br>0% I<br>0% M<br>0% P<br>0% W<br>0% Y | 20% DG<br>10% ALR<br>6% E<br>5% V<br>4% H<br>4% P<br>4% S<br>3% I<br>2% F<br>2% K<br>2% M<br>2% Q<br>2% T<br>2% Y<br>1% N<br>1% W<br>0% C | 20% G<br>15% D<br>10% AR<br>6% P<br>6% S<br>6% V<br>5% E<br>4% L<br>3% I<br>3% T<br>3% Y<br>2% F<br>2% H<br>2% K<br>2% N<br>2% Q<br>2% W<br>1% M<br>0% C | 15% GD<br>10% LPR<br>10% SV<br>6% E<br>5% A<br>6% T<br>4% Y<br>3% I<br>2% F<br>2% H<br>2% K<br>2% N<br>2% Q<br>1% C<br>1% M<br>1% W | 15% G<br>10% RDS<br>10% P<br>6% A<br>6% L<br>6% V<br>5% I<br>4% A<br>4% E<br>4% I<br>4% T<br>3% H<br>2% C<br>2% F<br>2% K<br>2% M<br>2% N<br>2% Q | 15% G<br>10% YSR<br>10% DP<br>6% L<br>5% T<br>5% A<br>4% F<br>4% T<br>3% E<br>3% F<br>2% C<br>2% E<br>2% H<br>2% K<br>2% N<br>2% Q<br>2% W<br>1% M | 15% YG<br>10% SDR<br>6% T<br>6% V<br>5% L<br>5% A<br>4% F<br>4% I<br>3% C<br>2% E<br>2% H<br>2% M<br>2% N<br>2% Q<br>2% W<br>1% K | 15% SY<br>10% GDV<br>6% A<br>5% L<br>5% R<br>5% T<br>4% C<br>4% F<br>4% I<br>4% P<br>3% W<br>2% E<br>2% N<br>2% Q<br>1% H<br>1% K<br>1% M | 15% SG<br>10% YDV<br>6% T<br>5% I<br>5% A<br>4% F<br>4% C<br>4% F<br>4% R<br>3% C<br>3% P<br>2% E<br>2% N<br>1% H<br>1% K<br>1% M<br>1% Q | 20% S<br>15% G<br>10% YV<br>6% T<br>5% A<br>5% D<br>6% V<br>5% R<br>5% W<br>4% F<br>4% I<br>4% L<br>3% N<br>3% P<br>2% C<br>2% E<br>1% H<br>1% K<br>1% M<br>1% Q | 20% G<br>15% S<br>10% Y<br>6% A<br>6% T<br>6% V<br>5% D<br>5% L<br>5% R<br>4% W<br>3% I<br>3% N<br>3% P<br>2% C<br>2% E<br>2% F<br>2% H<br>1% K<br>1% M | 20% Y<br>15% GS<br>6% V<br>5% A<br>5% R<br>5% T<br>4% D<br>4% L<br>4% P<br>3% C<br>3% I<br>3% N<br>3% W<br>2% E<br>2% F<br>2% Q<br>1% H<br>1% K<br>1% M |

| | Kabat-pos. | g | h | i | j | k | l | new | m | n | 101 | 102 |
|---|---|---|---|---|---|---|---|---|---|---|---|---|
| | AHO-pos. | 121 | 122 | 123 | 124 | 125 | 126 | 127 | 128 | 129 | 137 | 138 |
| | Name | | TRIM5 | | TRIM6 | | TRIM7 | | TRIM8 | | TRIM9 | TRIM10 | TRIM11 |
| | Design | | 30% Y<br>10% GS<br>5% PRDA<br>1.6% all | | | | 20% F<br>20% Y<br>10% GM<br>0.8% all | 35% D<br>10% FMY<br>5% GV<br>1.3% all | | 20% DV<br>10% IPYM<br>2.1% all | | 45% V<br>20% D<br>10% YI<br>5% PA<br>0.3% all | 65% V<br>11.6% IPY |
| | natural aa-distribution | 25% Y<br>10% GS<br>6% P<br>5% L<br>5% R<br>5% T<br>5% V<br>4% A<br>4% D<br>3% C<br>3% F<br>3% I<br>3% N<br>2% E<br>2% H<br>2% W<br>1% K<br>1% M<br>1% Q | 30% Y<br>10% GS<br>6% P<br>5% R<br>4% A<br>4% F<br>4% L<br>4% T<br>3% D<br>3% H<br>3% N<br>3% V<br>2% C<br>2% E<br>2% F<br>2% I<br>2% W<br>1% K<br>1% Q<br>0% M | 35% Y<br>10% GS<br>10% G<br>6% D<br>6% S<br>5% N<br>5% R<br>4% A<br>4% L<br>4% P<br>3% H<br>3% T<br>3% W<br>2% E<br>2% F<br>2% V<br>1% C<br>1% I<br>1% K<br>1% Q<br>0% M | 35% Y<br>15% G<br>10% A<br>5% N<br>5% P<br>5% W<br>4% D<br>4% R<br>4% S<br>3% T<br>2% F<br>2% H<br>2% L<br>2% V<br>1% E<br>1% I<br>1% K<br>0% C<br>0% M<br>0% Q | 25% F<br>20% Y<br>10% GM<br>6% A<br>4% L<br>2% W<br>3% D<br>2% N<br>2% P<br>2% S<br>2% T<br>1% H<br>1% I<br>1% R<br>1% V<br>0% C<br>0% E<br>0% K<br>0% Q | 40% D<br>15% F<br>10% MYG<br>3% A<br>2% L<br>1% E<br>1% H<br>1% I<br>1% N<br>1% P<br>1% S<br>1% T<br>1% V<br>0% C<br>0% K<br>0% R | 30% D<br>15% YV<br>10% FM<br>6% I<br>5% G<br>4% L<br>1% A<br>1% H<br>1% S<br>0% C<br>0% E<br>0% K<br>0% N<br>0% Q<br>0% R<br>0% T<br>0% W | 30% D<br>25% V<br>10% YMI<br>6% F<br>5% G<br>3% L<br>2% G<br>1% A<br>1% H<br>1% S<br>0% C<br>0% E<br>0% K<br>0% N<br>0% Q<br>0% R<br>0% T<br>0% W | 30% VD<br>20% YIP<br>6% M<br>3% F<br>3% L<br>1% H<br>1% K<br>1% Q<br>1% S<br>1% T<br>0% A<br>0% C<br>0% E<br>0% G<br>0% M<br>0% N<br>0% R<br>0% W | 45% V<br>20% D<br>10% YI<br>5% P<br>4% L<br>2% H<br>2% S<br>1% A<br>1% F<br>1% K<br>1% Q<br>0% C<br>0% E<br>0% G<br>0% M<br>0% N<br>0% R<br>0% T<br>0% W | 65% V<br>10% IPY<br>1% F<br>0% A<br>0% C<br>0% D<br>0% E<br>0% G<br>0% H<br>0% K<br>0% L<br>0% M<br>0% N<br>0% Q<br>0% R<br>0% S<br>0% T<br>0% W |

TABLE 13

Centered alignment of H-CDR3 regions with 15-23 aa lengths

| Kabat-pos. | 95 | 96 | 97 | 98 | 99 | 100 | a | b | c | d | e | f |
|---|---|---|---|---|---|---|---|---|---|---|---|---|
| AHO-pos. | 109 | 110 | 111 | 112 | 113 | 114 | 115 | 116 | 117 | 118 | 119 | 120 |
| Name | TRIM1 | TRIM2 | | | | TRIM3 | | | TRIM4 | | | TRIM5 |
| Design | 20% DG<br>8% | 10% G<br>10% | 15% GYS | | | | | | 15% SG<br>10% YV | | | 15% GSY<br>5% RAT |

TABLE 13-continued

Centered alignment of H-CDR3 regions with 15-23 aa lengths

|  | VEAS<br>1.5% all | RSLP<br>2.6%<br>all | 5% DRP<br>VALIT<br>0.8% all |  |  |  |  | 5% DT2,1<br>% all |  |  | VDL<br>1.3% all |  |
|---|---|---|---|---|---|---|---|---|---|---|---|---|
| natural<br>aa-<br>distribution | 25% D<br>20% G<br>10% AEV<br>6% S<br>4% L<br>4% R<br>3% H<br>2% I<br>2% P<br>2% Q<br>2% T<br>1% F<br>1% K<br>1% M<br>1% N<br>1% W<br>1% Y<br>0% C | 15% G<br>10% RPLS<br>5% A<br>5% V<br>4% D<br>4% I<br>4% Y<br>5% I<br>3% E<br>3% F<br>3% H<br>3% K<br>3% Q<br>3% T<br>2% M<br>2% N<br>2% Q<br>1% C | 15% G<br>10% YRS<br>6% L<br>6% P<br>6% V<br>5% A<br>5% I<br>5% T<br>4% A<br>4% D<br>3% E<br>2% C<br>2% F<br>2% H<br>2% K<br>2% N<br>2% Q<br>2% W<br>1% M | 15% YG<br>10% SDR<br>6% V<br>6% I<br>5% L<br>5% P<br>5% T<br>4% A<br>3% C<br>3% F<br>2% E<br>2% H<br>2% K<br>2% N<br>2% Q<br>2% W<br>1% M | 15% GY<br>10% SD<br>6% R<br>6% T<br>6% V<br>5% A<br>4% C<br>4% F<br>4% I<br>4% P<br>3% E<br>2% H<br>2% K<br>2% M<br>2% Q<br>1% H<br>1% K | 15% S<br>10% GYDV<br>6% A<br>6% T<br>4% F<br>4% I<br>4% P<br>4% R<br>4% W<br>3% L<br>2% C<br>2% E<br>2% M<br>2% N<br>1% H<br>1% K<br>1% Q | 20% S<br>15% G<br>10% YVD<br>6% T<br>5% A<br>5% F<br>5% I<br>5% L<br>4% W<br>3% C<br>3% P<br>3% R<br>2% N<br>1% E<br>1% H<br>1% K<br>1% M<br>1% Q | 15% G<br>10% SDT<br>10% VLY<br>6% A<br>6% C<br>4% A<br>4% F<br>4% I<br>4% R<br>3% E<br>3% P<br>2% N<br>1% K<br>1% M<br>1% Q<br>0% H | 20% S<br>10% GV<br>6% F<br>6% I<br>6% W<br>5% D<br>5% R<br>5% T<br>5% Y<br>4% C<br>4% P<br>4% R<br>3% E<br>3% L<br>2% N<br>1% H<br>1% K<br>1% Q<br>0% M | 20% S<br>15% G<br>10% YV<br>6% T<br>5% A<br>5% D<br>5% W<br>4% F<br>4% I<br>4% L<br>3% N<br>3% P<br>2% C<br>2% E<br>1% H<br>1% K<br>1% M<br>1% Q | 20% G<br>15% S<br>10% Y<br>6% A<br>6% T<br>6% V<br>5% D<br>5% L<br>5% R<br>4% W<br>3% I<br>3% N<br>3% P<br>2% C<br>2% E<br>2% F<br>2% H<br>1% K<br>1% M<br>1% Q | 20% Y<br>15% GS<br>6% V<br>5% A<br>5% R<br>5% T<br>4% D<br>4% L<br>4% P<br>3% C<br>3% I<br>3% N<br>3% W<br>2% E<br>2% F<br>2% Q<br>1% H<br>1% K<br>1% M |

| Kabat-pos. | g | h | i | j | k | l | new | m | n | 101 | 102 |
|---|---|---|---|---|---|---|---|---|---|---|---|
| AHO-pos. | 121 | 122 | 123 | 124 | 125 | 126 | 127 | 128 | 129 | 137 | 138 |
| Name | TRIM5 |  | TRIM6 |  |  | TRIM7 |  | TRIM8 | TRIM9 | TRIM10 wobble | TRIM11 |
| Design |  | 30% Y<br>10% GS<br>5%<br>PRD<br>1.8% all |  |  | 45% Y<br>7.5% S<br>GPR<br>1.3%<br>all |  | 40% Y<br>10%<br>GDN<br>1.6% all | 30% G<br>20% YA<br>10% W<br>5% P<br>0.8% all | 50% F<br>30% M<br>10% L<br>0.5% all | 80% D<br>20% A<br>(A for<br>peptide-<br>binders;<br>comment<br>AHO) | 40% V<br>20% Y<br>10% IP<br>4%<br>FHLMS |
| natural<br>aa-<br>distribution | 25%<br>Y<br>10%<br>GS<br>6% P<br>5% L<br>5% R<br>5% T<br>5% V<br>4% A<br>4% D<br>3% C<br>3% F<br>3% I<br>3% N<br>2% E<br>2% H<br>2% W<br>1% K<br>1% M<br>1% Q | 30%<br>Y<br>10%<br>GS<br>6% P<br>5% R<br>4% A<br>4% F<br>4% L<br>4% T<br>3% D<br>3% H<br>3% N<br>3% V<br>2% C<br>2% E<br>2% I<br>2% W<br>1% K<br>1% Q<br>0% M | 30%<br>Y<br>15%<br>N*<br>6% I<br>6% K<br>6% P<br>6% V<br>4% A<br>4% G<br>4% L<br>4% S<br>3% E<br>3% W<br>1% D<br>1% F<br>1% H<br>1% M<br>1% R<br>1% T<br>0% C<br>0% Q | 35%<br>Y<br>10%<br>PRS<br>10% DG<br>5% L<br>4% T<br>3% E<br>3% F<br>3% H<br>3% T<br>2% A<br>2% H<br>2% I<br>2% Q<br>2% E<br>1% C<br>1% K<br>1% M<br>1% V<br>1% W<br>0% N | 45% Y<br>10%<br>SG<br>6% R<br>5% P<br>4% L<br>3% A<br>3% N<br>3% T<br>2% D<br>2% E<br>2% F<br>2% H<br>2% K<br>2% V<br>2% W<br>1% I<br>1% Q<br>0% C<br>0% M | 45% Y<br>6% G<br>6% P<br>6% S<br>4% A<br>4% L<br>4% R<br>4% T<br>h<br>3% F<br>3% H<br>3% N<br>3% V<br>2% E<br>2% K<br>1% C<br>1% I<br>1% Q<br>1% W<br>0% M | 40% Y<br>10%<br>GDN<br>4% S<br>4% W<br>3% R<br>2% A<br>2% E<br>2% F<br>2% H<br>2% L<br>2% P<br>2% T<br>1% C<br>1% I<br>1% K<br>1% V<br>0% M<br>0% Q | 30% G<br>20% A<br>10% W<br>4% P<br>2% A<br>2% F<br>2% H<br>2% S<br>2% T<br>2% L<br>1% I<br>1% N<br>1% R<br>1% V<br>0% C<br>0% E<br>0% K<br>0% M | 50% F<br>35% M<br>10% L<br>2% I<br>2% V<br>1% G<br>1% P<br>1% S<br>1% T<br>1% D<br>0% A<br>0% C<br>0% E<br>0% H<br>0% K<br>0% N<br>0% Q<br>0% R<br>0% T<br>0% W | 95% D<br>1% E<br>1% G<br>1% Q<br>0% A<br>0% C<br>0% F<br>0% I<br>0% K<br>0% L<br>0% M<br>0% N<br>0% P<br>0% R<br>0% S<br>0% T<br>0% V<br>0% W<br>0% Y | 40% V<br>25% Y<br>10% IP<br>5% L<br>2% F<br>2% H<br>2% S<br>1% M<br>0% A<br>0% C<br>0% D<br>0% E<br>0% G<br>0% K<br>0% N<br>0% Q<br>0% R<br>0% T<br>0% W |

TABLE 14

Centered alignment of H-CDR3 regions with 15-23 aa lengths

| Kabat-pos. | 95 | 96 | 97 | 98 | 99 | 100 | a | b | c | d | e | f |
|---|---|---|---|---|---|---|---|---|---|---|---|---|
| AHO-pos. | 109 | 110 | 111 | 112 | 113 | 114 | 115 | 116 | 117 | 118 | 119 | 120 |
| Name | TRIM1 | TRIM2 |  |  |  | TRIM3 |  |  | TRIM4 |  | TRIM5 |  |
| Design | 20% DG<br>8%<br>VEAS<br>1.5% all | 10% G<br>10%<br>RSLP<br>2.6% all | 15%<br>GYS<br>5%<br>DRP<br>VALIT<br>0.8% all |  |  |  |  |  | 20% Y<br>15% G<br>10% S<br>2.9%<br>all |  | 30% Y<br>7.5%<br>GSPR<br>2.1% all |  |

TABLE 14-continued

Centered alignment of H-CDR3 regions with 15-23 aa lengths

| natural aa-distribution | | | | | | | | | | | |
|---|---|---|---|---|---|---|---|---|---|---|---|
| 25% D | 15% G | 15% G | 15% YG | 15% GY | 15% SG | 20% S | 15% GS | 20% Y | 20% Y | 30% Y | 30% Y |
| 20% G | 10% RPLS | 10% YRS | 10% SDR | 10% SD | 15% G | 15% YV | 10% YT | 15% GS | 15% G | 10% GSP | 10% GSP |
| 10% AEV | 5% A | 6% L | 6% V | 6% R | 6% A | 10% YV | 10% V | 6% R | 10% S | 5% L | 6% R |
| 6% S | 5% V | 6% P | 5% I | 6% T | 6% T | 6% D | 6% D | 6% V | 5% A | 4% A | 5% L |
| 4% L | 4% D | 6% V | 5% L | 6% V | 4% F | 6% T | 6% T | 5% A | 4% A | 4% I | 5% T |
| 4% I | 4% I | 5% A | 5% P | 5% A | 4% I | 5% A | 5% R | 5% T | 5% T | 4% N | 4% A |
| 4% R | 5% A | 5% I | 5% T | 5% T | 4% L | 4% F | 5% W | 4% D | 5% R | 4% R | 4% F |
| 3% H | 4% Y | 5% I | 4% A | 4% C | 4% L | 4% F | 4% L | 4% L | 5% T | 4% T | 4% V |
| 2% I | 3% E | 4% D | 3% C | 4% F | 4% R | 4% I | 3% C | 3% C | 5% V | 4% V | 3% D |
| 2% P | 3% F | 3% E | 3% F | 4% I | 4% W | 4% L | 3% I | 3% C | 4% C | 3% D | 3% H |
| 2% Q | 3% H | 2% C | 2% E | 4% L | 3% N | 4% R | 3% N | 3% I | 4% D | 3% F | 3% N |
| 2% T | 3% K | 2% F | 3% F | 4% P | 3% P | 3% N | 3% P | 3% N | 4% F | 2% C | 2% C |
| 1% F | 3% Q | 2% F | 2% H | 3% E | 2% C | 3% P | 2% E | 3% P | 4% P | 2% E | 2% E |
| 1% K | 3% T | 2% H | 2% K | 3% N | 2% E | 3% P | 3% P | 3% I | 2% E | 2% I | |
| 1% M | 2% M | 2% K | 2% N | 2% M | 2% M | 2% C | 2% F | 3% W | 3% W | 2% H | 2% I |
| 1% N | 2% N | 2% N | 2% Q | 2% Q | 1% H | 2% E | 2% H | 2% E | 2% E | 2% W | 2% Q |
| 1% W | 2% W | 2% Q | 2% W | 2% W | 1% K | 1% H | 1% K | 2% H | 2% H | 1% K | 1% K |
| 1% Y | 1% C | 2% W | 1% M | 1% H | 1% Q | 1% K | 1% M | 2% Q | 2% N | 1% Q | 1% W |
| 0% C | | 1% M | | 1% K | | 1% M | 1% Q | 1% K | 1% K | 0% M | 0% M |
| | | | | | | 1% Q | | 1% M | 1% Q | | |
| | | | | | | | | | 0% M | | |

| Kabat-pos. | g | h | i | j | k | l | new | m | n | 101 | 102 |
|---|---|---|---|---|---|---|---|---|---|---|---|
| AHO-pos. | 121 | 122 | 123 | 124 | 125 | 126 | 127 | 128 | 129 | 137 | 138 |
| Name | | TRIM5 | | TRIM6 | | TRIM7 | TRIM8 | TRIM4 | TRIM9 | wobble | TRIM10 |
| Design | | | 45% Y | | 55% Y | | 40% Y | 30% G | 50% F | 80% D | 40% V |
| | | | 7.5% GPRS | | 2.4% all | | 10% GDN | 20% YA | 30% M | 20% A | 20% Y |
| | | | 1.3% all | | | | 1.6% all | 10% W | 10% L | (A for peptide-binders; comment AHO) | 10% IP |
| | | | | | | | | 5% P | 0.5% all | | 4% FHLNS* |
| | | | | | | | | 0.8% all | | | |
| natural aa-distribution | 35% Y | 35% Y | 45% Y | 45% Y | 55% Y | 60% Y | 40% Y | 30% G | 50% F | 99% D | 40% V |
| | 10% GS | 10% GSP | 10% G | 10% PS | 10% G | 10% N | 10% GDN | 25% Y | 40% M | 1% E | 25% Y |
| | 6% P | 6% R | 6% P | 6% R | 4% F | 6% S | 4% S | 20% A | 10% W | 1% G | 10% IP |
| | 6% R | 5% D | 6% R | 4% D | 4% K | 4% G | 4% W | 10% W | 2% I | 1% Q | 5% L |
| | 5% A | 4% L | 5% S | 4% G | 3% A | 4% T | 3% R | 4% P | 2% V | 0% A | 2% F |
| | 5% T | 3% A | 4% L | 4% T | 3% D | 3% A | 2% A | 2% F | 1% G | 0% C | 2% H |
| | 4% L | 3% H | 3% A | 3% E | 3% L | 3% D | 2% E | 2% H | 1% P | 0% F | 2% S |
| | 3% D | 3% N | 3% N | 3% F | 3% N | 3% L | 2% F | 2% S | 1% S | 0% H | 1% M |
| | 3% N | 3% T | 3% T | 3% L | 3% P | 3% R | 2% H | 2% T | 1% Y | 0% I | 0% A |
| | 3% V | 2% E | 3% V | 2% A | 2% E | 1% H | 2% L | 2% D | 1% D | 0% K | 0% C |
| | 2% C | 2% F | 2% D | 2% H | 2% H | 1% P | 2% P | 1% D | 0% A | 0% L | 0% D |
| | 2% E | 2% I | 2% E | 2% I | 2% R | 1% Q | 2% T | 1% L | 0% C | 0% M | 0% E |
| | 2% F | 2% K | 2% F | 2% N | 2% S | 1% V | 1% C | 1% N | 0% D | 0% N | 0% G |
| | 2% H | 2% V | 2% H | 1% C | 2% T | 0% C | 1% I | 1% R | 0% H | 0% P | 0% K |
| | 2% I | 2% W | 2% I | 1% K | 2% V | 0% E | 1% K | 1% V | 0% K | 0% R | 0% N |
| | 2% K | 1% Q | 2% K | 1% Q | 1% I | 0% F | 1% V | 0% C | 0% N | 0% S | 0% Q |
| | 2% W | 0% C | 2% W | 1% V | 1% Q | 0% I | 0% C | 0% E | 0% Q | 0% T | 0% R |
| | 1% M | 0% M | 1% Q | 1% W | 1% W | 0% K | 0% M | 0% K | 0% R | 0% V | 0% T |
| | 1% Q | | 0% C | 0% M | 0% C | 0% Q | 0% Q | 0% M | 0% T | 0% W | 0% W |
| | | | 0% M | | 0% M | 0% W | | 0% Q | 0% W | 0% W | 0% Y |

TABLE 15

Centered alignment of H-CDR3 regions with 15-23 aa lengths

| Kabat-pos. | 95 | 96 | 97 | 98 | 99 | 100 | a | b | c | d | e | f |
|---|---|---|---|---|---|---|---|---|---|---|---|---|
| AHO-pos. | 109 | 110 | 111 | 112 | 113 | 114 | 115 | 116 | 117 | 118 | 119 | 120 |
| Name | TRIM1 | TRIM2 | TRIM3 | | | TRIM4 | | | TRIM5 | | | TRIM6 |
| Design | 20% DG | 10% G | 15% GR | 10% | 10% GYP | 10% | 15% G | | 15% GSYV | 15% G | 15% GY | 15% GSY |
| | 8% VEAS | 10% RSLP | 7.5% NPWS | GYP VRS | | 15% G | 10% SYVD | | 10% | 10% YSD | 10% SV | 10% V |
| | 1.5% all | 2.6% all | 2.1% all | 2.1% all | | 10% PRA | 5% R | | | | | 5% ADTRL |
| | | | | | | | 2.1% all | | | | | 1% all |
| natural aa-distribution | 25% D | 15% G | 20% G | 15% R | 10% GYLP | 10% GSY | 15% G | 10% GSYV | 15% G | 15% GY | 15% GY | 15% SG |
| | 20% G | 10% RPLS | 15% R | 10% GSY | 10% V | 10% PRA | 10% YRSD | 6% D | 10% YSD | 10% SV | 10% SV | 10% YV |
| | 10% AEV | 5% A | 10% NPW | 6% A | 10% R | 10% DTV | 6% P | 6% I | 6% L | 6% D | 6% A | 6% A |
| | 6% S | 5% V | 6% S | 5% D | 10% S | 4% E | 6% V | 6% R | 6% R | 6% R | 6% D | 6% D |

TABLE 15-continued

Centered alignment of H-CDR3 regions with 15-23 aa lengths

| | | | | | | | | | | | |
|---|---|---|---|---|---|---|---|---|---|---|---|
| 4% L | 4% D | 6% T | 5% N | 6% I | 4% I | 5% I | 5% L | 6% V | 6% T | 5% L | 6% T |
| 4% R | 4% I | 6% V | 5% P | 5% D | 3% C | 5% T | 5% T | 5% I | 5% A | 5% R | 5% L |
| 3% H | 4% Y | 6% Y | 5% T | 5% E | 3% L | 4% A | 4% A | 5% P | 5% P | 5% T | 5% R |
| 2% I | 3% E | 4% A | 4% E | 4% C | 2% F | 4% F | 4% P | 5% T | 4% F | 4% C | 4% I |
| 2% P | 3% F | 3% I | 4% I | 4% N | 2% H | 4% L | 3% C | 4% A | 4% I | 4% F | 4% P |
| 2% Q | 3% H | 3% K | 4% K | 3% F | 2% K | 3% E | 3% F | 4% F | 4% L | 4% I | 4% W |
| 2% T | 3% K | 3% L | 4% L | 3% T | 2% N | 3% N | 2% E | 3% W | 3% C | 4% P | 3% C |
| 1% F | 3% Q | 1% C | 3% V | 2% A | 2% Q | 2% C | 2% H | 2% C | 3% W | 3% W | 3% F |
| 1% K | 3% T | 1% D | 2% C | 2% K | 1% M | 2% H | 2% K | 2% E | 2% E | 2% E | 2% E |
| 1% M | 2% M | 1% F | 2% F | 2% M | 1% W | 2% K | 2% N | 2% H | 2% N | 2% N | 2% N |
| 1% N | 2% N | 1% Q | 2% M | 1% H | | 2% M | 2% W | 2% M | 2% Q | 1% H | 1% H |
| 1% W | 2% W | 0% E | 1% H | 1% Q | | 2% Q | 1% M | 2% N | 1% H | 1% K | 1% K |
| 1% Y | 1% C | 0% H | 1% Q | 0% W | | 1% W | 1% Q | 2% Q | 1% K | 1% M | 1% M |
| 0% C | | 0% M | 1% W | | | | | 1% K | 1% M | 1% Q | 1% Q |

| Kabat-pos. | g | h | i | j | k | l | new | m | n | 101 | 102 |
|---|---|---|---|---|---|---|---|---|---|---|---|
| AHO-pos. | 121 | 122 | 123 | 124 | 125 | 126 | 127 | 128 | 129 | 137 | 138 |
| Name Design | | TRIM6 | 15% YGS 5% PRDTA 1.6% all | TRIM7 | 40% Y 10% S G 2.1% all | | TRIM8 40% Y 10% GDN 1.6% all | TRIM9 30% G 20% YA 10% W 5% P 0.8% all | TRIM10 50% F 30% M 10% L 1% all | TRIM11 wobble 80% D 20% A 10% Y 10% L (A for peptide-binders; comment AHO) | TRIM12 40% V 20% Y 10% IP 4% FHLMS |
| natural aa-distribution | 15% GS 10% Y 6% A 6% R 6% T 6% V 5% D 5% I 4% F 4% L 4% W 3% P 2% C 2% E 2% N 1% H 1% K 1% M 1% Q | 15% GS 10% Y 6% A 6% R 6% T 6% V 5% A 5% D 5% L 4% P 4% W 3% F 3% I 3% N 2% C 2% E 2% K 1% H 1% M 1% Q | 15% GYS 6% D 6% V 5% A 5% P 5% R 4% C 4% L 4% N 3% I 3% W 2% C 2% E 2% F 2% H 2% Q 1% K 1% M | 25% Y 10% GS 6% P 5% R 5% T 4% A 4% C 4% D 4% L 4% V 3% I 3% N 2% E 2% F 2% H 2% I 2% Q 2% W 1% K 0% M | 35% Y 10% GS 6% P 5% R 4% A 4% L 4% T 4% V 3% F 2% C 2% D 2% E 2% H 2% I 2% N 2% W 1% K 1% Q 0% M | 40% Y 10% SG 5% P 5% T 4% A 4% F 4% L 4% N 4% R 3% D 3% H 3% V 2% T 2% E 2% I 2% W 1% K 1% Q 0% M | 40% Y 10% GDN 4% S 4% W 3% R 2% A 2% E 2% F 2% H 2% L 2% P 1% C 1% I 1% K 1% V 0% M 0% Q | 30% G 25% Y 20% A 10% W 4% P 2% F 2% M 2% S 2% T 1% D 1% I 1% L 1% N 1% R 1% V 0% C 0% E 0% K 0% M 0% Q | 50% F 35% M 10% L 2% I 2% V 1% G 1% P 1% S 1% Y 0% A 0% C 0% D 0% E 0% H 0% K 0% N 0% Q 0% R 0% T 0% W | 95% D 1% E 1% G 1% Q 0% A 0% C 0% F 0% H 0% I 0% K 0% L 0% M 0% P 0% R 0% S 0% T 0% V 0% W 0% Y | 40% V 25% Y 10% IP 5% L 2% F 2% H 2% S 1% M 0% A 0% C 0% D 0% E 0% G 0% K 0% N 0% Q 0% R 0% T 0% W |

In another non-limiting example, the present invention provides for a collection of diverse H-CDR3 regions of varying length, wherein diversity of the H-CDR3 regions can be generated by diversifying H-CDR3 regions having a length within a first range of amino acids of about 4 to about 8 amino acids according to a first diversity factor, where the first diversity factor requires that: Alanine has a frequency rate of about 80% at position 1, Arginine has a frequency rate of about 60% at position 2. Glycine has a frequency rate of about 40% at position 3, Aspartic acid has a frequency rate of about 50% at position 7 and Tyrosine has a frequency rate of about 40% at position 8 (table 16).

TABLE 16 the table shows an example for a diversity factor for diversifying H-CDR3 regions having a length within a first range of amino acids of about 4 to about 8 amino acids.

aa Postion HCDR3

| 1 | 2 | 3 | 4 | 5 | 6 | 7 | 8 |
|---|---|---|---|---|---|---|---|
| A 80 | R 60 | G 40 | 19 w/o C | 19 w/o C | 19 w/o C | D 50 | Y 40 |
| T 10 | 18 w/o Cys | 18 w/o Cys | | | | G 10 | V 20 |
| 17 w/o Cys | | | | | | A 10 | 17 w/o Cys |
| | | | | | | 16 w/o C | |

In another non-limiting example, the present invention provides for a collection of diverse human or humanized antibody H-CDR3 regions of varying length, wherein diversity of the H-CDR3 regions can be generated by diversifying H-CDR3 regions having a length within a first range of amino acids of about 9 to about 15 amino acids according to a first diversity factor, where the first diversity factor requires that: Alanine has a frequency rate of about 90% at position 1, Arginine has a frequency rate of about 70% at position 2, Tyrosine has a frequency rate of about 20% at position 10, Tyrosine has a frequency rate of about 20% at position 11, Tyrosine has a frequency rate of about 30% at position 12, Phenylalanine has a frequency rate of about 60% at position 13, Aspartic acid has a frequency rate of about 80% at position 14 and Tyrosine has a frequency rate of about 40% at position 15. Preferably, the diversity of a human or humanized H-CDR3 region having an amino acid length of about 9 to about 15 amino acids is generated by a high content of Glycine and Serine inside the H-CDR3 region (table 17).

| aa Position HCD3 | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| | A90 | R70 | G20 | R15 | G20 | G20 | G20 | G20 | G20 | Y20 | Y20 | Y30 | F60 | D80 | Y40 |
| | T5 | K20 | D20 | G15 | S10 | S10 | S10 | S10 | S10 | G10 | G20 | G20 | L10 | 18 w/o C | V20 |
| | V5 | 17 w/o C | 17 w/o C | 17 w/o C | 17 w/o C | Y10 | Y10 | Y10 | Y10 | S10 | S10 | A10 | 17 w/o C | | P10 |
| | | | | | | 16 w/o C | 16 w/o C | 16 w/o C | 16 w/o C | 16 w/o C | 16 w/o C | 16 w/o C | | | 16 w/o C |

In yet another non-limiting embodiment, the present invention provides for a collection of diverse human or humanized antibody H-CDR3 regions of varying length, wherein diversity of the H-CDR3 regions can be generated by diversifying H-CDR3 regions having a length of about 16 to about 22 amino acids according to a first diversity factor, where the first diversity factor requires that: Alanine has a frequency rate of about 90% at position 1, Arginine has a frequency rate of about 60% at position 2, Aspartic acid has a frequency rate of about 30% at position 3, Glycine has a frequency rate of about 20% at position 4, Arginine has a frequency rate of about 10% at position 5, Arginine has a frequency rate of about 10% at position 6, Tyrosine has a frequency rate of about 20% at position 7, Tyrosine has a frequency rate of about 40% at position 15, Tyrosine has a frequency rate of about 50% at position 16, Tyrosine has a frequency rate of about 50% at position 17, Tyrosine has a frequency rate of about 60% at position 18, Tyrosine has a frequency rate of about 40% at position 19, Methionine has a frequency rate of about 50% at position 20, Aspartic acid has a frequency rate of about 95% at position 21 and Valine has a frequency rate of about 60% at position 22 (table 18).

TABLE 18 the table shows an example for a diversity factor for diversifying H-CDR3 regions having a length within a first range of amino acids of about 16 to about 22 amino acids.
as Position HCD3

| 1 | 2 | 3 | 4 | 5 | 6 | 7 | 8 | 9 | 10 | 11 | 12 |
|---|---|---|---|---|---|---|---|---|---|---|---|
| A 90 | R 60 | D 30 | G 20 | R 10 | R 10 | Y 20 | S 20 | R 10 | G 20 | S 20 | S 20 |
| T 5 | K 20 | G 20 | P 10 | P 10 | Y 10 | G 10 | G 10 | D 10 | D 10 | G 10 | Y 10 |
| V 5 | T 20 | 17 w/o C | R 10 | G 10 | G 10 | P 10 | I 10 | G 10 | 17 w/o C | V 20 | G 10 |
| | | | F 10 | F 10 | I 10 | M 10 | Y 10 | V 10 | | 16 w/o C | V 10 |
| | | | 15 w/o C | 15 w/o C | 15 w/o C | 15 w/o C | 15 w/o C | 15 w/o C | | | 15 w/o C |

| 13 | 14 | 15 | 16 | 17 | 18 | 19 | 20 | 21 | 22 |
|---|---|---|---|---|---|---|---|---|---|
| E 10 | Y 20 | Y 40 | Y 50 | Y 50 | Y 60 | Y 40 | M 50 | D 95 | V 60 |
| S 10 | T 10 | G 10 | G 10 | 18 w/o C | 18 w/o C | G 40 | F 40 | Q 5 | 16 w/o C |
| G 10 | 17 w/o C | 17 w/o C | 17 w/o C | | | 17 w/o C | 17 w/o C | | |
| 16 w/o C | | | | | | | | | |

Furthermore, the diversity of a collection of human or humanized H-CDR3 regions having an amino acid length of about 16 to about 22 amino acids can be generated by a high content of serine in the H-CDR3 region, a high content of basic amino acids in the end part (C-terminal) of the H-CDR3 region, aspartic acid in the front part (N-terminal) of the HCDR3 region and a high content of aromatic amino acid over the whole H-CDR3 region.

In the context of the present invention, it is understood that at any given amino acid position in an H-CDR3 region, the occurrence of amino acids not specified with a defined frequency rate at a defined amino acid position can occur in substantially equal ratios vis-à-vis each other, or some amino acids may have a higher frequency rate compared to other amino acids at such position and, in some cases, certain amino acids may be omitted at one or more defined amino acid positions (e.g. Cysteine).

In the context of the present invention, the design of diverse H-CDR3 regions can be done by mimicking the known natural distribution of amino acids by biasing the complete random distribution of amino acids in the H-CDR3 encoding DNA sequence. The generation of diverse H-CDR3 regions can be done by using the trinucleotide mutagenesis (TRIM) technology (Virnekäs et al., 1994), which allows synthesizing any desired mixture of amino acids at will at each single position, thereby introducing any amino acid bias at any position. Generally, the TRIM technology relies on using pre-assembled trinucleotides as input for standard DNA synthesis, thereby avoiding frameshifts, stop codons, or undesired amino acids and yields enormous sequence diversity. Therefore, very large library sizes are required to generate a broad enough functional sequence space. Correspondingly, the knowledge of the length-dependent amino acid composition in combination with the TRIM technology should allow a design of a much smaller collection of H-CDR3 regions with much higher functional content.

In another aspect, the present invention provides for a collection of diverse human or humanized antibody variable heavy chains comprising a collection of diverse H-CDR3 regions, wherein diversity of each H-CDR3 region is generated by diversifying H-CDR3 regions having a length within a first range of amino acids according to a first diversity factor and by diversifying H-CDR3 regions having a length within a second range of amino acids by a second diversity factor, where each diversity factor is a function of the amino acid length of each H-CDR3 region. Furthermore, the invention provides for a collection of diverse human or humanized antibodies or functional fragments thereof, each of which contains a human or humanized antibody variable heavy chain according to the invention. In the context of the present invention, it is to be understood that for the generation of a collection of diverse human or humanized antibodies or functional fragments thereof, the skilled artisan will be able to modify the theoretical design of a collection of diverse H-CDR3 regions. The skilled worker will appreciate that it may be acceptable to modify the design with respect to amino acids occurring at a low frequency rate (e.g. aa of a frequency below 5% or preferably below 3%), by adding those amino acids appearing below such frequency rate in equimolar concentrations vis-à-vis each other, for example; thus, collections of diverse human or humanized antibodies or functional fragments thereof may be generated by including mixtures of such amino acids at such concentrations.

In another aspect, the present invention provides for a synthetic human or humanized antibody library comprising a collection of diverse human or humanized antibodies or functional fragments thereof. The synthetic consensus sequences may cover the structural repertoire of antibodies encoded in the human genome. A synthetic human or humanized antibody library may be based on antibodies or antibody fragments, preferably Fv, disulphide-linked Fv, single chain Fv (scFv), or Fab fragments, which may be used as sources of specificities against new target antigens.

In the context of the present invention, a synthetic human or humanized antibody library may be based on amino acid sequences that have been designed in silico and encoded by nucleic acids that are synthetically created. In silico design of an antibody sequence is achieved, for example, by analyzing a database of human sequences and devising a polypeptide sequence utilizing the data obtained therefrom. By analyzing the known germline amino acid sequences of human immunoglobulin variable domains, antibody genes are grouped into sub-families according to the sequence homology and canonical structures (Chothia et al., 1992; Tomlinson et al., 1995). Due to the high homology in terms of amino acid sequence and canonical structures within one sub-family, 7 VH and 7 VL consensus sequences (master genes) can be designed and combined to yield 49 master framework combinations (Knappik et al., 2000). The master genes could be chemically synthesized thereby generating a completely modular gene structure by introducing unique restriction sites flanking all functional modules.

Methods for designing and obtaining in silico-created sequences are described, for example, in Knappik et al., J. Mol. Biol. (2000) 296:57; Krebs et al., J. Immunol. Methods. (2001) 254:67; and U.S. Pat. No. 6,300,064 issued to Knappik et al., which hereby are incorporated by reference in their entirety.

In another aspect, the present invention provides for methods of preparing a collection of nucleic acid molecules encoding diverse human or humanized H-CDR3 regions. This can be done, for example, by synthesizing a plurality of DNA molecules, where each encodes an H-CDR3 region, and where the H-CDR3 regions are of varying ranges. To this end, the DNA molecules that encode H-CDR3 regions of a first range of amino acids are synthesized according to a first diversity factor and DNA molecules encoding H-CDR3 regions of a second range of amino acids are synthesized according to a second diversity factor, the diversity factors being different.

In one aspect, the present invention provides for a collection of nucleic acids encoding a collection of diverse human or humanized antibody H-CDR3 regions of varying ranges of amino acids, wherein diversity of the collection is generated by diversifying H-CDR3 regions having a length within a first range of amino acids according to a first diversity factor and by diversifying H-CDR3 regions having a length within a second range of amino acids according to a second diversity factor, wherein the diversity factors are different.

Also provided within the present invention are methods of obtaining a collection of diverse human or humanized antibody H-CDR3 regions. This can be accomplished by expressing the collection of nucleic acids encoding a collection of diverse human or humanized antibody H-CDR3 regions according to the present invention.

In another aspect, the present invention provides for methods of identifying one or more genes encoding one or more H-CDR3 regions of the invention which bind to a given target. This is accomplished, e.g., by expressing the H-CDR3 regions, and then screening them to isolate one or more H-CDR3 regions which bind to a given target molecule. An H-CDR3 region may be comprised within an antibody variable heavy chain. Screening may be performed by using one of the methods well known to the practitioner in the art, such as phage display or CysDisplay (described, e.g., in U.S. Pat. No. 6,753,136).

In the context of the present invention, a human or humanized antibody library may be based on the combination of gene fragments from human donors with designed synthetic DNA. As an example, human-donor-sourced fragments encoding the light chain variable region and a range of the heavy chain region are combined with synthetic DNA encoding human antibody sequences with diversity introduced at specific sites.

The invention also provides for mutated or optimized antibodies (or fragments thereof) derived from an antibody or fragment thereof, as disclosed herein. An antibody is composed of two peptide chains, each containing one (light chain) or three (heavy chain) constant domains and a variable region (VL, VH), the latter of which is in each case made up of four FR regions and three interspaced CDRs. The antigen-binding site is formed by one or more CDRs, yet the FR regions provide the structural framework for the CDRs and can also play an important role in antigen binding. By altering one or more amino acid residues in a CDR or FR region, the skilled worker routinely can generate mutated or diversified antibody sequences, which can be screened against the antigen, for new or improved properties, for example.

Also, as used herein, an "immunoglobulin" (Ig) hereby is defined as a protein belonging to the class IgG, IgM, IgE, IgA, or IgD (or any subclass thereof), and includes all conventionally known antibodies and functional fragments thereof. A "functional fragment" of an antibody/immunoglobulin hereby is defined as a fragment of an antibody/immunoglobulin (e.g., a variable region of an IgG) that retains the antigen-binding region. An "antigen-binding region" of an antibody typically is found in one or more hypervariable region(s) of an antibody, i.e., the CDR-1, -2, and/or -3 regions; however, the variable "framework" regions can also play an important role in antigen binding, such as by providing a scaffold for the CDRs. Preferably, the "antigen-binding region" comprises at least amino acid residues 4 to 103 of the variable light (VL) chain and 5 to 109 of the variable heavy (VH) chain, more preferably amino acid residues 3 to 107 of VL and 4 to 111 of VH, and particularly preferred are the complete VL and VH chains (amino acid positions 1 to 109 of VL and 1 to 113 of VH; numbering according to WO 97/08320). A preferred class of immunoglobulins for use in the present invention is IgG. "Functional fragments" of the invention include the domain of a F(ab')2 fragment, a Fab fragment and scFv. The F(ab')2 or Fab may be engineered to minimize or completely remove the intermolecular disulphide interactions that occur between the CH1 and CL domains.

The term "hypervariable region" when used herein refers to the amino acid residues of an antibody which are responsible for antigen-binding. The hypervariable region comprises amino acid residues from a "complementarity determining region" or "CDR" (i.e. residues 24-34 (L1), 50-56 (L2) and 89-97 (L3) in the light chain variable domain and 31-35 (H1); 50-65 (H2) and 95-102 (H3) in the heavy chain variable domain; Kabat et al., Sequences of Proteins of Immunological Interest, 5th Ed. Public Health Service, National Institutes of Health, Bethesda, Md. (1991)) and/or those residues from a "hypervariable loop" (i.e. residues 26-32 (L1), 50-52 (L2) and 91-96 (L3) in the light chain variable domain and 26-32 (H1), 53-55 (H2) and 96-101 (H3) in the heavy chain variable domain; Chothia and Lesk J. Mol. Biol. 196:901-917 (1987)). "Framework" or "FR" residues are those variable domain residues other than the hypervariable region residues as herein defined.

A "human" antibody or functional human antibody fragment is hereby defined as one that is not chimeric (e.g., not "humanized") and not from (either in whole or in part) a non-human species. A human antibody or functional antibody fragment can be derived from a human or can be a synthetic human antibody. A "synthetic human antibody" is defined herein as an antibody having a sequence derived, in whole or in part, in silico from synthetic sequences that are based on the analysis of known human antibody sequences. In silico design of a human antibody sequence or fragment thereof can be achieved, for example, by analyzing a database of human antibody or antibody fragment sequences and devising a polypeptide sequence utilizing the data obtained therefrom. Another example of a human antibody or functional antibody fragment is one that is encoded by a nucleic acid isolated from a library of antibody sequences of human origin (i.e., such library being based on antibodies taken from a human natural source).

A "humanized antibody" or functional humanized antibody fragment is defined herein as one that is (i) derived at least in part from a non-human source (e.g., a transgenic mouse which bears a heterologous immune system), which antibody is based on a human germline sequence; or (ii) chimeric, wherein at least a portion of the variable domain is derived from a non-human origin and the constant domain is derived from a human origin or (iii) CDR-grafted, wherein at least a portion of the CDRs of the variable domain are from a non-human origin, while one or more frameworks of the variable domain are of human origin and the constant domain (if any) is of human origin.

The invention claimed is:

1. A collection comprising diverse, isolated human or humanized antibody H-CDR3 regions, wherein the H-CDR3 regions comprise a first, second and third range of amino acid lengths, wherein the first range consists of 4 to 7 amino acids in length, wherein the amino acids of the first range of lengths comprise diversity according to a first diversity factor, wherein the second range consists of 8 to 14 amino acids in length, wherein the amino acids of the second range of lengths comprise diversity according to a second diversity factor, and wherein the third range consists of 15 to 23 amino acids in length, wherein the amino acids of the third range of lengths comprise diversity according to a third diversity factor, wherein the diversity factors comprise a frequency rate at which amino acids appear at each position in the H-CDR3 region, and wherein the first, second and third diversity factors are different, wherein the H-CDR3 regions consisting of a length of 4 amino acids comprise at position 1 Aspartic acid and Glycine have a frequency rate of about 25, Valine, Glutamic acid, Alanine, Leucine, Arginine and Serine have a frequency rate of about 5%, all other amino acids except Cysteine have a frequency rate of about 1.1%; at position 2 Arginine, Glycine, Serine and Tyrosine have a frequency rate of about 10%, Alanine, Aspartic acid, Histidine, Isoleucine and Threonine have a frequency rate of about 5% and all other amino acids except Cysteine have a frequency rate of about 1.8%; at position 3 Glycine has a frequency rate of about 25%, Tyrosine, Serine, Aspartic Acid and Arginine have a frequency rate of about 10% and all other amino acids except Cysteine have a frequency rate of about 1.8%; and at position 4 Glycine has a frequency rate of about 25%, Tyrosine, Serine, and Alanine have a frequency rate of about 10% and all other amino acids except Cysteine have a frequency rate of about 2.4%.

2. A collection according to claim 1, wherein the H-CDR3 regions consisting of a length of 4 to 7 amino acids in length comprise at position 1 Glycine and Aspartic acid have a frequency rate of about 25%, Alanine, Glutamic acid, Valine, Leucine, Arginine and Serine have a frequency rate of about 5% and all other amino acids except Cysteine have a frequency rate of about 1.1%; at position 2 Arginine, Glycine, Serine and Tyrosine have a frequency rate of about 10%, Alanine, Aspartic acid, Histidine, Isoleucine and Threonine have a frequency rate of about 5% and all other amino acids except Cysteine have a frequency rate of about 1.8%; at position 3 Glycine has a frequency rate of about 25%, Tyrosine, Serine, Aspartic Acid and Arginine have a frequency rate of about 10% and all other amino acids except Cysteine have a frequency rate of about 1.8%; at position 4 Glycine has a frequency rate of about 25%, Tyrosine, Serine, and Alanine have a frequency rate of about 10% and all other amino acids except Cysteine have a frequency rate of about 2.4%; at position 5 Phenylalanine has a frequency rate of about 30%, Leucine has a frequency rate of about 15%, Methionine and Glycine have a frequency rate of about 10% and all other amino acids except Cysteine have a frequency rate of about 1.8%; at position 6 Aspartic Acid has a frequency rate of about 65%, Glycine has a frequency rate of about 10% and all other amino acids except Cysteine have a frequency rate of about 1.3%; and at position 7 Tyrosine has a frequency rate of about 50%, Valine has a frequency rate of about 15%, Isoleucine has a frequency rate of about 10% and all other amino acids except Cysteine have a frequency rate of about 1.3%.

3. A collection according to claim 1, wherein the H-CDR3 regions consisting of a length of 8 to 14 amino acids in length comprise at position 1 Glycine and Aspartic acid have a frequency rate of about 20%, Alanine, Glutamic acid, Valine, and Serine have a frequency rate of about 8% and all other amino acids except Cysteine have a frequency rate of about 1.5%; at position 2 Glycine, Arginine, Serine, Leucine and Proline have a frequency rate of about 10%, and all other amino acids except Cysteine have a frequency rate of about 2.6%; at positions 3, 4, 5, 6 and 7 Glycine, Tyrosine and Serine have a frequency rate of about 15%, Aspartic acid, Arginine, Proline, Valine, Alanine, Leucine, Isoleucine and Threonine have a frequency rate of about 5% and all other amino acids except Cysteine have a frequency rate of about 0.8%, that at position 8, 9 and 10 Tyrosine has a frequency rate of about 20%, Glycine has a frequency rate of about 15%, Serine has a frequency rate of about 10% and all other amino acids except Cysteine have a frequency rate of about 2.9%; at position 11 Tyrosine and Alanine have a frequency rate of about 20%, Glycine has a frequency rate of about 15%, Tryptophan has a frequency rate of about 10%, Proline has a frequency rate of about 5% and all other amino acids except Cysteine have a frequency rate of about 2.6%; at position 12 Phenylalanine has a frequency rate of about 50%, Methionine and Leucine have a frequency rate of about 10% and all other amino acids except Cysteine have a frequency rate of about 1.6%; at position 13 Aspartic acid has a frequency rate of about 80% and Alanine has a frequency rate of about 20%; and at position 14 Tyrosine has a frequency rate of about 45%, Valine and Isoleucine have a frequency rate of about 15%, Proline has a frequency rate of about 10% and Phenylalanine, Histidine, Leucine, Asparagine and Serine have a frequency rate of about 3%.

4. A collection according to claim 1, wherein the H-CDR3 regions consisting of a length of 15 to 23 amino acids in length comprise at position 1 Glycine and Aspartic acid have a frequency rate of about 20%, Alanine, Glutamic acid, Valine, and Serine have a frequency rate of about 8% and all other amino acids except Cysteine have a frequency rate of about 1.5%; at position 2 Glycine, Arginine, Serine, Leucine and Proline have a frequency rate of about 10%, and all other amino acids except Cysteine have a frequency rate of about 2.6%; at positions 3, 4, 5, 6, 7 and 8 Glycine, Tyrosine and Serine have a frequency rate of about 15%, Aspartic acid, Arginine, Proline, Valine, Alanine, Leucine, Isoleucine and Threonine have a frequency rate of about 5% and all other amino acids except Cysteine have a frequency rate of about 0.8%; at positions 9 and 10 Tyrosine has a frequency rate of about 20%, Glycine has a frequency rate of about 15%, Serine has a frequency rate of about 10% and all other amino acids except Cysteine have a frequency rate of about 2.9%; at positions 11, 12, 13 and 14 Tyrosine has a frequency rate of about 30%, Glycine, Serine, Proline and Arginine have a frequency rate of about 7.5% and all other amino acids except Cysteine have a frequency rate of about 2.1%; at positions 15 and 16 Tyrosine has a frequency rate of about 45%, Glycine, Serine, Proline and Arginine have a frequency rate of about 7.5% and all other amino acids except Cysteine have a frequency rate of about 1.3%; at positions 17 and 18 Tyrosine has a frequency rate of about 55%, and all other amino acids except Cysteine have a frequency rate of about 2.4%; at position 19 Tyrosine has a frequency rate of about 40%, Glycine, Aspartic acid, and Asparagine have a frequency rate of about 10% and all other amino acids except Cysteine have a frequency rate of about 1.6%; at position 20 Glycine has a frequency rate of about 30%, Tyrosine and Alanine have a frequency rate of about 20%, Tryptophan has a frequency rate of about 10%, Proline has a frequency rate of about 5% and all other amino acids except Cysteine have a frequency rate of about 0.8%; at position 21 phenylalanine has a frequency rate of about 50%, Methionine has a frequency rate of about 30%, Leucine has a frequency rate of about 10% and all other amino acids except Cysteine have a frequency rate of about 0.5%; at position 22 Aspartic acid has a frequency rate of about 80% and Alanine has a frequency rate of about 20%; and at position 23 Valine has a frequency rate of about 40%, Tyrosine has a frequency rate of about 20%, Isoleucine and Proline have a frequency rate of about 10% and Phenylalanine, Histidine, Leucine, Asparagine and Serine have a frequency rate of about 4%.

5. A collection of diverse human or humanized antibody variable heavy chains comprising a collection of diverse human or humanized antibody H-CDR3 regions according to claim 1.

6. A collection of diverse human or humanized antibodies or functional fragments thereof, comprising the collection of diverse human or humanized antibody H-CDR3 regions according to claim 1.

7. A synthetic human or humanized antibody library, comprising a collection of diverse human or humanized antibodies or functional fragments thereof according to claim 6.

* * * * *